US012638431B2

(12) United States Patent
Carter et al.

(10) Patent No.: US 12,638,431 B2
(45) Date of Patent: May 26, 2026

(54) SYSTEM FOR AIR COMPOSITION ESTIMATION

(71) Applicant: Aeternum, LLC, Dulles, VA (US)

(72) Inventors: Paul Carter, Paeonian Springs, VA (US); Rosemary Carter, Paeonian Springs, VA (US); Sebastian Carter, Paeonian Springs, VA (US); Rikard Lundqvist, Ashburn, VA (US)

(73) Assignee: Aeternum, LLC, Dulles, VA (US)

( * ) Notice: Subject to any disclaimer, the term of this patent is extended or adjusted under 35 U.S.C. 154(b) by 342 days.

(21) Appl. No.: 18/200,961

(22) Filed: May 23, 2023

(65) Prior Publication Data

US 2024/0393307 A1      Nov. 28, 2024

(51) Int. Cl.
*G01N 33/00* (2006.01)
*G01D 21/02* (2006.01)
*G08B 21/12* (2006.01)

(52) U.S. Cl.
CPC ......... *G01N 33/0063* (2013.01); *G01D 21/02* (2013.01); *G08B 21/12* (2013.01)

(58) Field of Classification Search
CPC ............... G01D 21/02; G01N 33/0063; G01N 2015/0046; G01N 15/00; G01N 33/0031; G01N 33/0004; G01N 33/0062; G01N 15/06; G01N 15/075; G01N 15/1429; G01N 33/0075; G01N 1/2273; G01N 15/0205; G01N 15/1459; G01N 1/26; G01N 15/0266; G01N 15/0656; G01N 15/1425; G01N 15/149; G01N 2015/1477; G01N 33/0032; G01N 33/0065; G01N 2015/1486; G01N 33/0068; G06F 17/16; G06F 16/215;
(Continued)

(56) References Cited

U.S. PATENT DOCUMENTS 9,857,301 B1     1/2018   Nourbakhsh et al.
11,906,415 B1 *  2/2024   Galburt ............. G01N 15/1459
(Continued)

FOREIGN PATENT DOCUMENTS

GB      2610948 A      3/2023
WO   2017089020 A1   6/2017

OTHER PUBLICATIONS

Sep. 30, 2024—Extended European Search Report—App 24177468. 6.

*Primary Examiner* — Catherine T. Rastovski
*Assistant Examiner* — Eric Sebastian Von Wald
(74) *Attorney, Agent, or Firm* — Banner & Witcoff, Ltd.

(57) ABSTRACT
Aspects of the disclosure relate to an environment analysis platform for air composition estimation. The environment analysis platform may receive a set of environment information corresponding to an environment from one or more environment information sources. The environment analysis platform may generate an estimated air composition using an environment analysis model. The environment analysis platform may generate a cumulative particle score based on the estimated air composition. The environment analysis platform may determine whether or not the cumulative particle score satisfies a criteria. The criteria may indicate whether the environment is a compliant environment or an outlier environment. The environment analysis platform may send one or more commands directing a user device to display a user interface based on the determination.

20 Claims, 12 Drawing Sheets

(58) Field of Classification Search
CPC .... G06F 16/2365; G06F 18/24; G06F 18/285;
G06Q 10/04; G06Q 10/0838; G06V
10/87; G06V 20/695; G06V 20/698;
G08B 21/12
See application file for complete search history.

(56) References Cited

U.S. PATENT DOCUMENTS

| | | | |
|---|---|---|---|
| 2019/0277822 A1 | 9/2019 | Chadha et al. | |
| 2022/0341863 A1* | 10/2022 | Wakana | G01N 27/12 |
| 2023/0298451 A1* | 9/2023 | Bistany | G08B 21/12 |
| | | | 340/603 |

* cited by examiner

200

209

602

609

610

611

810

820

Environmental Hazard Notification Interface

Welcome, <User Device Profile>

Alert: Air Quality Anomaly Detected

Location: ABC Office Building, Sensor 001

Anomaly: PM1 level outside expected band

Alert Additional Devices?

Yes    No

SYSTEM FOR AIR COMPOSITION ESTIMATION

BACKGROUND

Aspects of the disclosure relate to performing air composition estimation using a device or system of devices. In some instances, sensors may be used to gather information corresponding to an environment (e.g., a geographical region, a building interior, and/or other environments). In some examples, based on the gathered information, individuals or organizations might desire to know specifically what particles are included in the air composition of the environment. Accordingly, it may be important to improve the efficiency of air composition estimation. Additionally, over time the air composition may change. Accordingly, it may also be important to identify methods for incorporating such changes into the air composition estimation process.

SUMMARY

Aspects of the disclosure provide effective, efficient, scalable, and convenient technical solutions that address and overcome the technical problems associated with environment analysis. In accordance with one or more embodiments of the disclosure, a computing platform with at least one processor, a communication interface, and memory storing computer-readable instructions may receive a set of environment information corresponding to an environment from one or more environment information sources. The set of environment information may include one or more measured variables corresponding to one or more attributes of a known particle, and/or one or more additional environment variables. The computing platform may generate an estimated air composition using an environment analysis model. The computing platform may generate a cumulative particle score based on the estimated air composition. The computing platform may further determine whether or not the cumulative particle score satisfies a criteria. The criteria may indicate whether the environment is a compliant environment or an outlier environment. The computing platform may send one or more commands directing a user device to display a user interface, based on the determination. The user interface may include a notification indicating a result of the determination.

As a brief description of the concepts described further herein, to solve the limitations and technical problems associated with environment analysis, some aspects of the disclosure relate to a system for air composition estimation. Individuals or organizations might desire to know which particles are included in the air composition of a particular environment. In order to identify the air composition, one or more environment information sources (e.g., sensors, satellites, detectors, and/or other information sources) may be implemented in order to gather environment information of the particular environment. In some instances, one or more types of particles included in the air composition (e.g., one or more specific gas molecules, one or more specific particulates, one or more specific types of dust, one or more specific biological contaminants, and/or one or more other types of particles) may be difficult to identify. Accordingly, a system may include one or more particle sensors configured to identify the one or more environment variables corresponding to one or more attributes of a known particle, in order to identify the one or more types of particles.

In these instances, the system may further include a computing platform configured to identify, using an environment analysis model (i.e., a machine learning model) and based on the variables corresponding to one or more attributes of a known particle, the types of particles detected by the particle sensors and generate an estimated air composition. The environment analysis model may be configured to take the variables as inputs. Additionally, the environment analysis model may be configured to take additional environment information (e.g., wind speed, wind direction, vibration information, and/or other information) as inputs. In some examples, the computing platform may receive the additional environment information from sources of environment information different from the particle sensors.

These features, along with many others, are discussed in greater detail below.

BRIEF DESCRIPTION OF THE DRAWINGS

The present disclosure is illustrated by way of example and not limited in the accompanying figures in which like reference numerals indicate similar elements and in which.

DETAILED DESCRIPTION

In the following description of various illustrative embodiments, reference is made to the accompanying drawings, which form a part hereof, and in which is shown, by way of illustration, various embodiments in which aspects of the disclosure may be practiced. In some instances, other embodiments may be utilized, and structural and functional modifications may be made, without departing from the scope of the present disclosure.

It is noted that various connections between elements are discussed in the following description. It is noted that these connections are general and, unless specified otherwise, may be direct or indirect, wired or wireless, and that the specification is not intended to be limiting in this respect.

Figure 1:
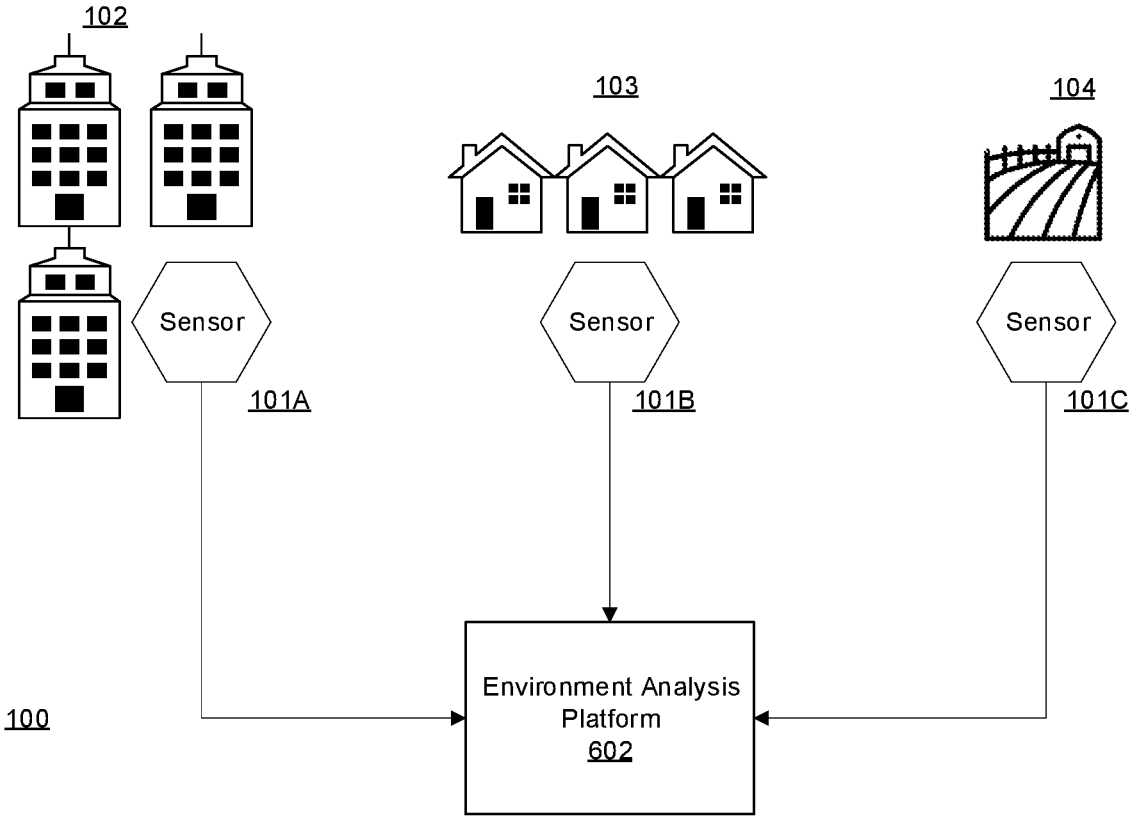
FIG. 1 depicts an illustrative environment information network for gathering information corresponding to an environment and sending the information to a computing platform for air composition estimation in accordance with one or more example embodiments.

FIG. 1 depicts an illustrative environment information network for gathering information corresponding to an environment and sending the information to a computing platform (e.g., an environment analysis platform, such as environment analysis platform 602) for air composition estimation. Referring to FIG. 1, environment information network 100 may include one or more environment information sources. For example, environment information network 100 may include one or more particle sensors configured to gather variables. The one or more particle sensors may be deployed in a geographical region. For example, one or more particle sensors, such as first particle sensor 101A, may be deployed in urban region 102 (e.g., a city, town, industrial district, and/or other urban regions). In some examples, the one or more particle sensors may be deployed to one or more different geographical regions. For example, a first particle sensor 101A might be deployed in urban region 102, while one or more particle sensors such as second particle sensor 101B may be deployed in residential region 103 (e.g., a neighborhood, residential district, apartment complex, and/or other residential regions). Additionally or alternatively, in some instances, one or more particle sensors such as third particle sensor 101C may be deployed in rural region 104 (e.g., a farm, preservation, forest, road, and/or other rural regions).

In some examples, the one or more environment information sources may be communicatively coupled (e.g., via a wireless data connection) with a computing platform (e.g., for estimating air composition). For example, first particle sensor 101A, second particle sensor 101B, third particle sensor 101C, and/or other environment information sources may be communicatively coupled to environment analysis platform 602. Each of 101A, 101B, and 101C may each represent multiple particle sensors. In some examples, the computing platform may receive environment information (e.g. periodically, continuously, near continuously) from each of the environment information sources. For example, environment analysis platform 602 may continuously receive environment information from each of first particle sensor 101A, second particle sensor 101B, and third particle sensor 101C. In other instances, the computing platform may only receive environment information from an environment information source at times the environment information source is considered "active" (e.g., when the environment information source is powered on, when the environment information source is actively gathering environment information, when the environment information source is actively transmitting environment information, and/or other times the environment information source may be considered "active").

The environment information gathered by the one or more environment information sources and received by the computing platform may include one or more measured variables corresponding to one or more attributes of a known particle, and/or one or more additional environment variables. The one or more additional environment variables may include one or more of: wind speed, wind direction, particle concentrations, gas concentrations, temperature, relative humidity, air pressure, dew point, vibration frequency, noise level, ventilation status, altitude, topographical information, occupancy, traffic count, mold growth information, mildew growth information, population information, luminosity information, precipitation information, or virus detection information. In some instances, a single environment information source (e.g., first particle sensor 101A, and/or other environment information sources) may gather a set of environment information. For example, first particle sensor 101A may gather both a measured particle count and a measured particle size.

Figure 2A:
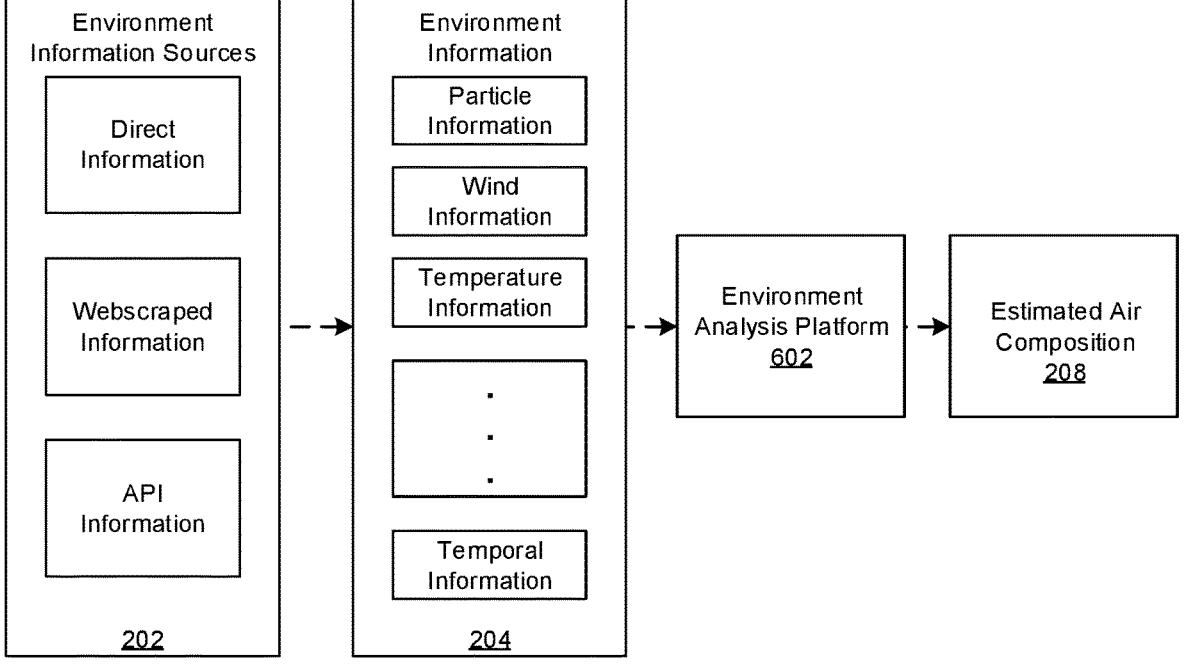
FIG. 2A depicts an illustrative event flow for air composition estimation using an environment analysis model in accordance with one or more example embodiments.

FIG. 2A depicts an illustrative event flow for air composition estimation using an environment analysis model. Referring to FIG. 2A, one or more environment information sources 202 may be configured to gather environment information 204 corresponding to a particular environment and send the environment information to the environment analysis platform 602. The one or more environment information sources 202 may be or include one or more of: a particle sensor, a network of particle sensors located at different geographical locations, a repository of information gathered by multiple unassociated sensors, satellites gathering environmental information, a repository of automotive traffic information (e.g., a repository of information gathered by one or more of cameras, radar sensors, lidar sensors, road cables, and/or other sources of traffic information), one or more particle sensors gathering environment information 204 of the interior of a building, one or more devices gathering environment information 204 from a moving vehicle, one or more anemometers, or a database corresponding to an environment analysis organization. In some examples, the one or more environment information sources may be configured to send the environment information 204 directly to the environment analysis platform 602. Additionally or alternatively, in some instances the one or more environment information sources may be configured to indirectly send the environment information 204 to the environment analysis platform 602. For example, the one or more environment information sources may send the environment information 204 to a repository (e.g., a web-based server, database, cloud storage system, and/or other repositories). In these examples, the environment analysis platform 602 may retrieve the environment information from the repository (e.g., via webscraping methods, application programming interface (API) calls, information transfer requests, and/or other methods).

Figure 3:
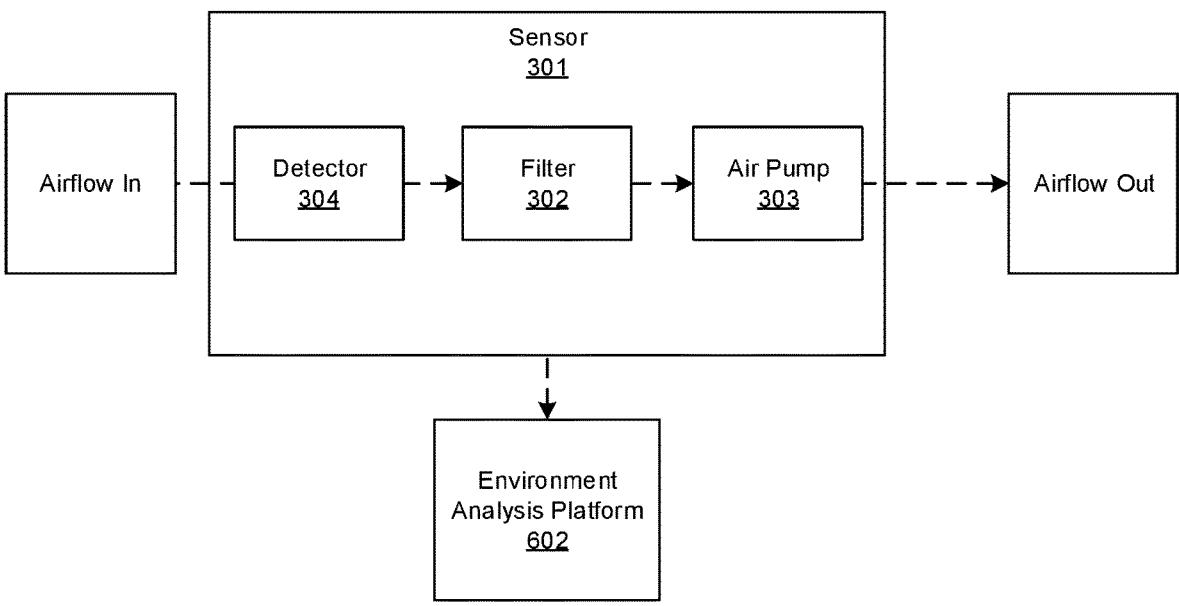
FIG. 3 depicts an illustrative system for gathering variable information using a sensor in accordance with one or more example embodiments.

The environment information sources 202 may gather the environment information 204 corresponding to the particular environment. The environment information sources 202 may gather the environment information 204 by using cameras, lasers, filtration devices, anemometers, and/or other methods. In some instances, the environment information sources 202 may gather the environment information 204 by collecting and analyzing particles (which may, e.g., include one or more of: gas molecules, particulates, dusts, biological contaminants, aerosols, and/or other types of particles) in the air of the environment (e.g., by equipping a particle sensor with a filter to capture particles, such as in system 300, as illustrated in FIG. 3, and/or by other methods). The environment information 204 gathered by the one or more environment information sources 202 and received by the environment analysis platform 602 may include one or more measured variables corresponding to one or more attributes of a known particle, and/or one or more additional environment variables. The one or more additional environment variables may include one or more of: wind speed, wind direction, particle concentrations, gas concentrations, temperature information, relative humidity information, air pressure information, dew point information, vibration information, noise information, environment ventilation status, altitude information, topographical information, occupancy information, traffic counts, mold growth information, mildew growth information, population information, luminosity information, precipitation information, and/or virus detection information.

Figure 4:
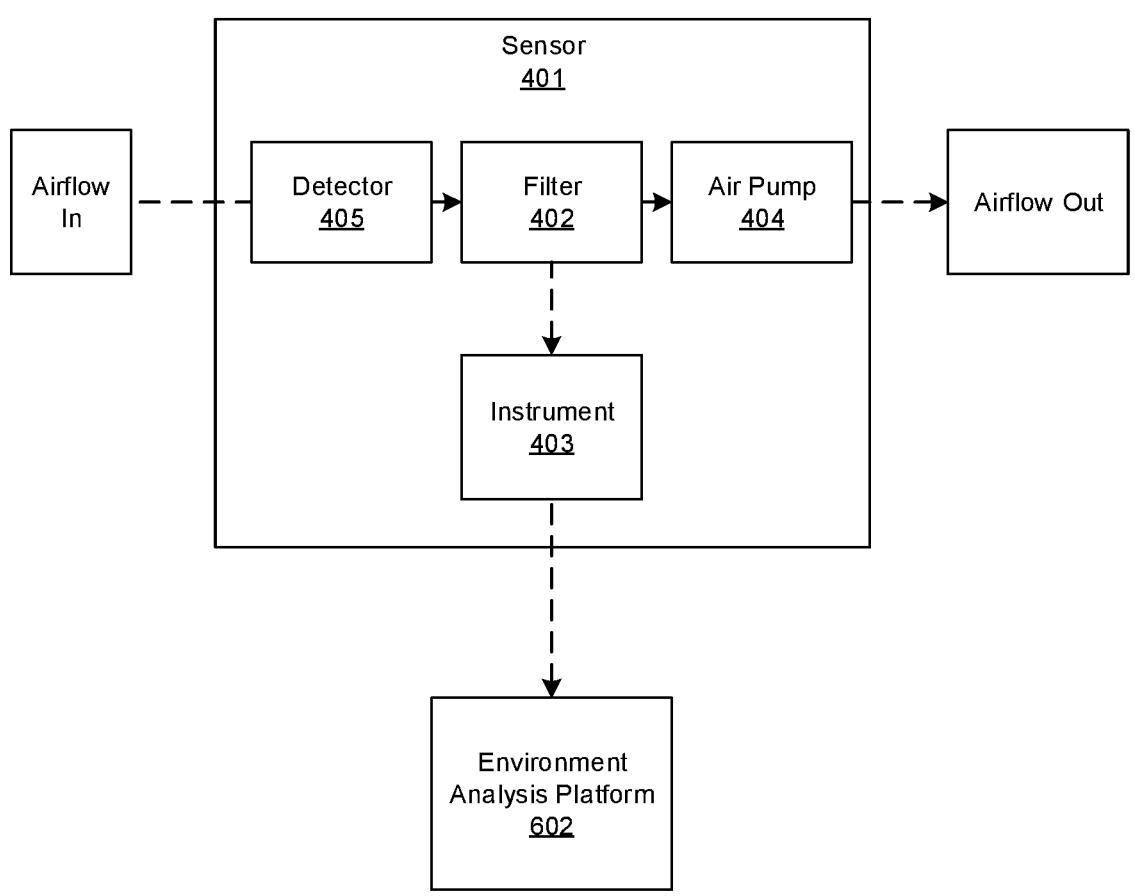
FIG. 4 depicts an illustrative system for gathering particle composition information using a sensor in accordance with one or more example embodiments.

Additionally or alternatively, in some instances, the additional environment variables may include information indicating compositions of particles. For example, the environment analysis platform 602 may be configured to receive environment information from an electronic microscope. In this example, particles in the air of the environment being analyzed may be gathered (e.g., by a particle sensor equipped with a filter for catching particles, such as in system 400, which is illustrated at FIG. 4, and/or by other methods).

Figure 6A:
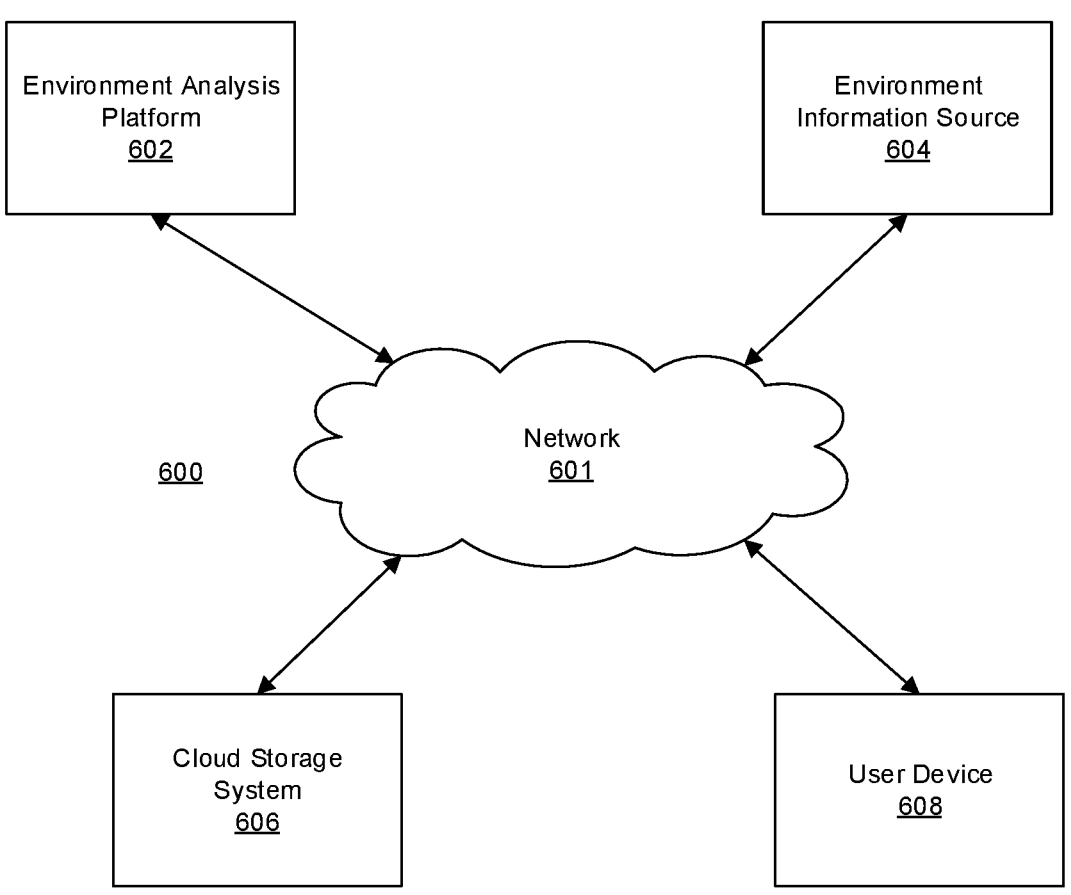
FIGS. 6A-6B depict illustrative computing systems in accordance with one or more example embodiments.
Figure 6B:
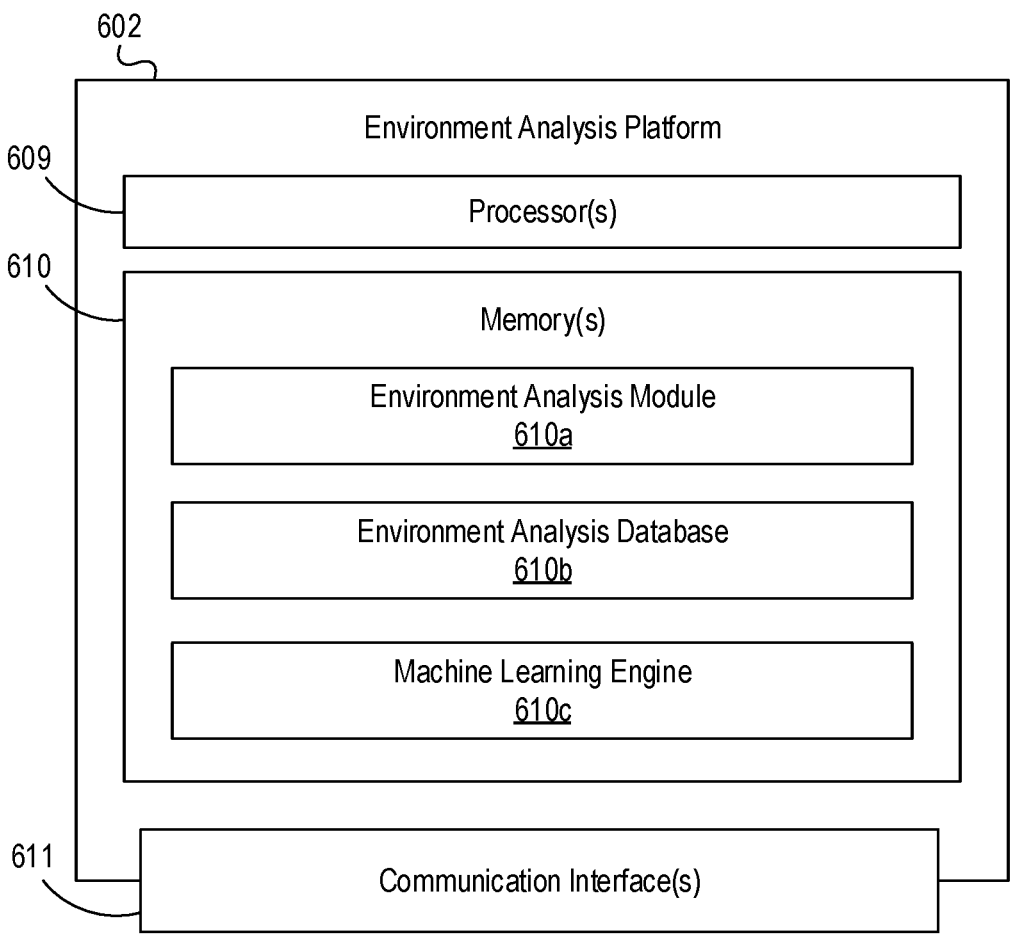

The environment analysis platform 602 may receive the environment information 204 from the environment information sources 202 via one or more wired or wireless data connections which may, e.g., be established via a communication interface communicatively coupled to the environment analysis platform 602 (e.g., communication interface 611, as illustrated in FIG. 6B, and/or other communication interfaces).

The environment analysis platform 602 may generate an estimated air composition 208 based on the environment information. For example, the environment analysis platform 602 may generate the estimated air composition that identifies specific particle types and/or concentrations of specific particle types based on the environmental information (e.g., particle size, particle count and/or other variables) using an environment analysis model (e.g., using the method illustrated in FIG. 7 and described below at step 706). The specific particle types may be and/or include one or more types of gas molecule (e.g., carbon dioxide molecules, carbon monoxide molecules, and/or other gas molecules), one or more types of particulate (e.g., aerosol particles, soot, tobacco smoke, smog, oil smoke, fly ash, and/or other particulates), one or more types of dust (e.g., cement dust, atmospheric dust, heavy dust, and/or other types of dust), one or more types of biological contaminant (e.g., pollen, mold spores, bacteria, viruses, and/or other biological contaminations) and/or other specific particle types. Creation of the environment analysis model may employ machine learning as illustrate in FIG. 2B.

Figure 2B:
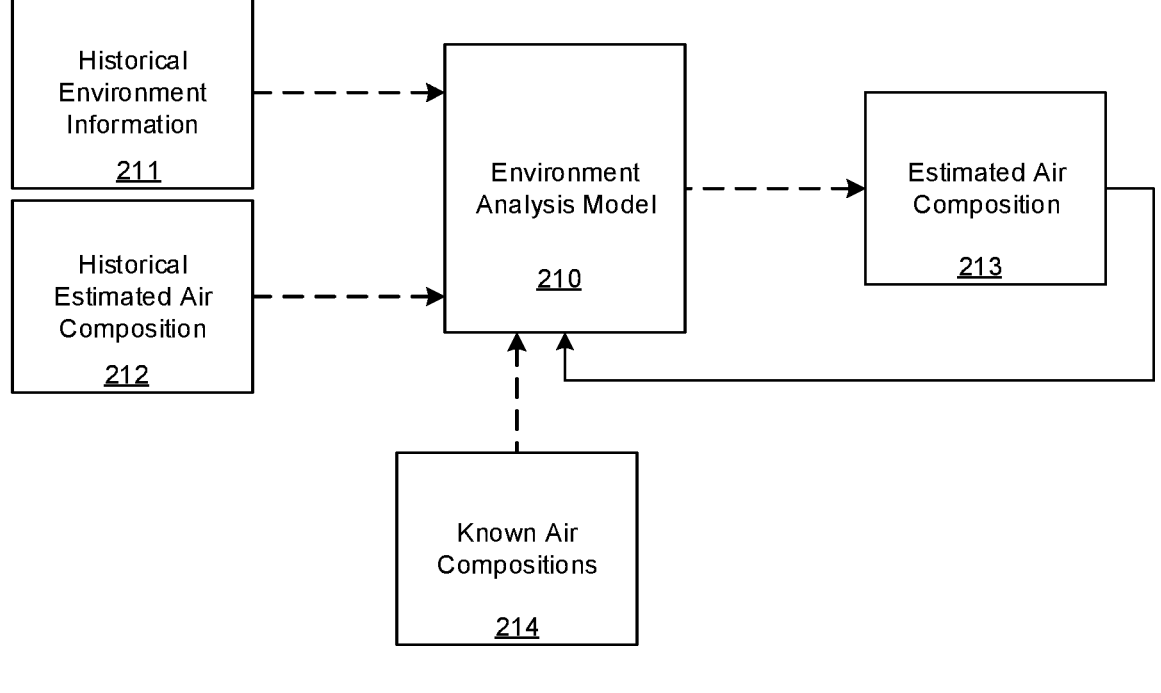
FIG. 2B depicts an illustrative event flow for training an environment analysis model in accordance with one or more example embodiments.

FIG. 2B depicts an illustrative event flow for training an environment analysis model 210. Referring to FIG. 2B, environment analysis model training 209 may include training the environment analysis model 210 to generate an estimated air composition 213 based on environment information. In some examples, environment analysis platform 602 may train the environment analysis model 210. In other examples, the environment analysis model training 209 may be performed by another computing platform. In some instances, the environment analysis platform 602 may configure and/or otherwise train the environment analysis model based on historical sets of environment information 211 (e.g., wind speed, wind direction, gas concentration information, temperature, relative humidity, air pressure, dew point, vibration frequency, noise level, ventilation status, altitude, topographical information, occupancy, traffic counts (such as a historical number of motor vehicles passing through the environment in a given timeframe, a historical number of motor vehicles present in the environment at a specific time, a volume of traffic, the direction of traffic flow, vehicle type (e.g., cars, vans, hybrid models, electric models, diesel models, and/or other vehicle types) and/or other traffic counts), mold growth information, mildew particulate information, population information (such as the occupancy of a building, a number of individuals detected by a recording device, a number of individuals within a proximity to a sensor, a volume of individuals within a specified location, a number of individuals passing through an area in a specified time window, and/or other population counts), luminosity information (such as light intensity, one or more solar angles detected by a sensor, cloud cover levels, and/or other luminosity information), precipitation information (such as a volume of precipitation over a period of time, a type of precipitation (e.g., snow, rain, sleet, and/or other types of precipitation), and/or other precipitation information) and/or virus detection information) and historical estimated air compositions 212 corresponding to the historical sets of environment information 211. In some examples, the historical sets of environment information 211 may also include one or more particle counts, one or more particle concentrations, one or more particle sizes, one or more specific particles and particles types (such as the specific particles and particle types listed above), and/or other particle identification information. In some instances, to configure and/or otherwise train the environment analysis model 210, environment analysis platform 602 may process all (or a subset) of the historical sets of environment information 211 and historical estimated air compositions 212 by applying natural language processing, natural language understanding, supervised machine learning techniques (e.g., regression, classification, neural networks, support vector machines, random forest models, naïve Bayesian models, and/or other supervised techniques), unsupervised machine learning techniques (e.g., principal component analysis, hierarchical clustering, K-means clustering, and/or other unsupervised techniques), and/or other techniques. In doing so, the environment analysis platform 602 may train the environment analysis model 210 to generate, for a particular environment, an estimated air composition 213.

For example, in configuring and/or otherwise training the environment analysis model 210, environment analysis platform 602 may input historical sets of environment information 211 that environment analysis platform 602 has previously performed air composition estimation operations on, and historical estimated air compositions 212 generated while performing those operations, into the environment analysis model 210. For instance, the environment analysis platform 602 may use as a training set, a historical set of environment information 211 that corresponds to a particular historical estimated air composition 212. The environment analysis platform 602 may train the environment analysis model to minimize a difference between historical estimated air composition 212 and a generated estimated air composition 213. Sets of historical environment information 211 and corresponding historical estimated air compositions 212 may have been obtained by other environment analysis models and/or by manual collection and analysis, and may be based on different geographical locations, and/or different time periods of the same location. Additionally or alternatively, the environment analysis platform 602 may mine the historical sets of environment information and historical estimated air compositions to determine common estimated air compositions for specific environment information. For example, based on the historical sets of environment information and the corresponding historical estimated air compositions, the environment analysis platform 602 may identify that all historical sets of environment information including a particular particle size correspond to a particular estimated air composition. In another instance, the environment analysis platform 602 may identify a particular estimated air composition corresponding to a particular source of environment information, based on the historical sets of environment information and the corresponding historical estimated air compositions. For example, the environment analysis platform 602 may identify that multiple instances of a particular estimated air composition (or a portion of the particular estimated air composition, e.g., a specific particle type among a plurality of particle types) appear in the historical estimated air compositions and correspond to a common source of environment information (e.g., a specific particle sensor, a specific satellite, and/or other sources of environment information). In these instances, the environment analysis platform 602 may train the environment analysis model to generate the particular estimated air composition (or portion of the particular estimated air composition) for the particular source of environment information.

In some instances, to configure and/or otherwise train the environment analysis model, environment analysis platform 602 may update (e.g., continually) the environment analysis model 210 in order to improve the accuracy of the environment analysis model. For example, in configuring and/or otherwise training the environment analysis model 210, environment analysis platform 602 may, after using the environment analysis model to generate an estimated air composition 213, input the estimated air composition 213 and a known air composition 214 corresponding to the same environment into the environment analysis model. By inputting the estimated air composition into the model, the environment analysis platform 602 may create an iterative feedback loop that may continuously and dynamically update the environment analysis model to improve its accuracy. In these instances, the known air composition 214 may have been gathered and/or otherwise confirmed by a user of the environment analysis platform 602 (e.g., for the purpose of training the environment analysis model). For example, individuals (e.g., employees of an environment analysis enterprise, and/or other individuals) may gather and subsequently analyze the particles gathered by sensors (e.g., 101) using an instrument or process (e.g., electronic microscope, spectrum analyzer, chemical reaction, and/or other instruments or processes). In analyzing the particles, the instrument or process may identify the composition of the particles and/or other identifiable features of the particles. Information about the particles (e.g., the composition of the particles and/or other features of the particles) may be generated by the instrument or process (e.g., electronic microscope), and that information may be sent (e.g., by wireless data transfer) to the environment analysis platform 602 for input to the model as known air composition 214. In some instances, the known air composition 214 may be or include a historical estimated air composition confirmed by the user of environment analysis platform 602. The environment analysis model may generate, based on the estimated air composition 213 and the known air composition 214, an error score indicating a margin of error between the estimated air composition and the known air composition.

In generating the error score, the environment analysis model may compare the estimated air composition 213 to the historical estimated air composition 212 and/or to the known air composition 214 in order to determine the margin of error. For example, the estimated air composition 213 and the known air composition 214 may be or include a number of identified particle types and particle counts corresponding to each of the identified particle types. The environment analysis model may compare the estimated number of identified particle types and particle counts to the known number of identified particle types and particle counts to determine the error score between the estimated air composition and the known air composition (e.g., by using root mean squared error calculations, mean squared error calculations, binary classification models, multiclass classification models, and/or other methods of calculating error). Based on the error score, the environment analysis platform

602 may update the environment analysis model to minimize the error. For example, the environment analysis platform 602 may identify whether or not the error score exceeds a threshold. Based on identifying that the error score does exceed the threshold, the environment analysis platform 602 may update the environment analysis model. In some examples of updating the environment analysis model, the environment analysis platform 602 may input additional historical environment information 211, corresponding historical estimated air compositions 213, and/or known air compositions 214 to configure and/or otherwise further train the environment analysis model (e.g., by using the methods described above) to more accurately estimate air compositions based on environment information.

FIG. 3 depicts an illustrative system 300 of gathering measured variables using a sensor for air composition estimation using an environment analysis model. Referring to FIG. 3, system 300 may include a sensor 301 connected (e.g., wired or wirelessly, permanently or momentarily) to the environment analysis platform 602 (e.g., for sending environment information). Sensor 301 may be a sensor device designed to generate environment information corresponding to an environment surrounding sensor 301 (e.g., a particle sensor designed to generate particle size and particle count measurements, and/or other sensor devices). Sensor 301 may generate the environment information by analyzing particles in air flowing through a detector 304 (e.g., by using cameras, lasers, and/or other methods of analyzing particles). The sensor 301 may be connected to the environment analysis platform 602 via a wired or wireless data connection (which may, e.g., be established via the communication interface 611). In some instances, the sensor 301 may be configured to receive airflow in from an environment and output airflow out from the sensor 301 after analyzing one or more particles captured while taking airflow in.

In some examples, sensor 301 may be further configured and/or otherwise constructed to include a filter 302. Filter 302 may be or include a filter medium (e.g., a surface media (such as a wire screen), a depth media (e.g., compressed felt), and/or other media). Filter 302 may capture particles from air flowing into sensor 301 using one or more particle capture methods (e.g., direct interception, inertial impaction, Brownian diffusion, hydrodynamic effects, electrostatic attraction, and/or other methods). Filter 302 may be installed and/or otherwise mechanically coupled with sensor 301 via a filter cartridge, and/or other coupling techniques. In some instances, filter 302 may be a reusable and/or multi-use filter. In some examples, filter 302 may be configured to be removed from sensor 301. In these examples, the filter 302 may be removed from the sensor 301 by a user of environment analysis platform 602 (e.g., an employee of an environment analysis enterprise, and/or other individuals) to evaluate the captured particles to confirm the accuracy of the environment information sent to environment analysis platform 602 by the sensor 301 (e.g., by analyzing the particles in a laboratory setting, by comparing the filter 302 to other filters, and/or by other methods). The evaluated information may be used as known air compositions 214 as discussed above with respect to FIG. 2B for training an environment analysis model.

Additionally or alternatively, sensor 301 may be further configured and/or otherwise constructed to include an air pump 303. Air pump 303 may be or include a device designed to generate airflow in (e.g., by operating a fan, a piston, and/or other methods of generating airflow) and produce airflow out. Air pump 303 may be installed and/or otherwise mechanically coupled to the sensor 301. Air pump 303 may operate continuously and/or operate on a configurable timer configurable by a user (e.g., an employee of an environment analysis enterprise, and/or other individuals). While detector 304, filter 302, and air pump 303 are illustrated in a particular order, these components can be arranged in any order, and detector 304 and filter 302 may be arranged adjacent or parallel to one another such that the air that flows through each is different.

FIG. 4 depicts another illustrative system of gathering particle composition information using a sensor for air composition estimation using an environment analysis model. Referring to FIG. 4, a system 400 may include a sensor 401 connected to the environment analysis platform 602 (e.g., for sending environment information). Sensor 401 may be a sensor device similar to sensor 301 and designed to generate environment information corresponding to an environment surrounding sensor 401 (e.g., a particle sensor designed to generate particle size and particle count measurements, and/or other sensor devices). Sensor 401 may generate the environment information by analyzing particles in air flowing through a detector 405 (e.g., by using cameras, lasers, and/or other methods of analyzing particles). The sensor 401 may be connected to the environment analysis platform 602 via a wired or wireless data connection (which may, e.g., be established via the communication interface 611). In some instances, the sensor 401 may be configured to receive airflow in from an environment and output airflow from the sensor 401 after analyzing one or more particles captured while taking airflow in.

In some examples, sensor 401 may be further configured and/or otherwise constructed to include a filter 402. Filter 402 may be or include a filter medium (e.g., a surface media (such as a wire screen), a depth media (e.g., compressed felt), and/or other media). Filter 402 may capture particles from air flowing into sensor 401 using one or more particle capture methods (e.g., direct interception, inertial impaction, Brownian diffusion, hydrodynamic effects, electrostatic attraction, and/or other methods). Filter 402 may be installed and/or otherwise mechanically coupled with sensor 401 via a filter cartridge, and/or other coupling techniques. In some instances, filter 402 may be a reusable and/or multi-use filter. In some examples, filter 402 may be configured to be removed from sensor 401. In these examples, the filter 402 may be removed from the sensor 401 by a user of environment analysis platform 602 (e.g., an employee of an environment analysis enterprise, and/or other individuals) to evaluate the captured particles to confirm the accuracy of the environment information sent to environment analysis platform 602 by the sensor 401 (e.g., by analyzing the particles in a laboratory setting, by using an electronic microscope, and/or by other methods). The evaluated information may be used as known air compositions 214 as discussed above with respect to FIG. 2*b* for training an environment analysis model.

In some instances, system 400 may additionally include an instrument 403 (e.g., spectrum analyzer, electronic microscope). Instrument 403 may be an electronic instrument which may, e.g., be low-powered and configured to analyze the particle composition of particles (e.g., by using transmission electron microscopy, scanning electron microscopy, spectrum analysis and/or other methods). In some examples, filter 402 may capture particles from the air flowing into sensor 401, which may be analyzed by instrument 403. In these examples, filter 402 may be mechanically coupled to instrument 403 and adapted to transfer the captured particles to the instrument. Based on analyzing the captured particles, instrument 403 may determine the composition of the captured particles. The sensor 401 may include the composition of the captured particles in the environment information sent to environment analysis platform 602.

Additionally or alternatively, sensor 401 may be further configured and/or otherwise constructed to include an air pump 404. Air pump 404 may be or include a device designed to generate airflow in (e.g., by operating a fan, a piston, and/or other methods of generating airflow) and produce airflow out. Air pump 404 may be installed and/or otherwise mechanically coupled to the sensor 401. Air pump 404 may operate continuously and/or operate on a configurable timer configurable by a user (e.g., an employee of an environment analysis enterprise, and/or other individuals). While detector 405, filter 402, instrument 403, and air pump 404 are illustrated in a particular order, these components can be arranged in any order, and detector 405 and filter 402 may be arranged adjacent or parallel to one another such that the air that flows through each is different. Additionally, detector 405 may not be included, or may be combined with instrument 403.

Figure 5:
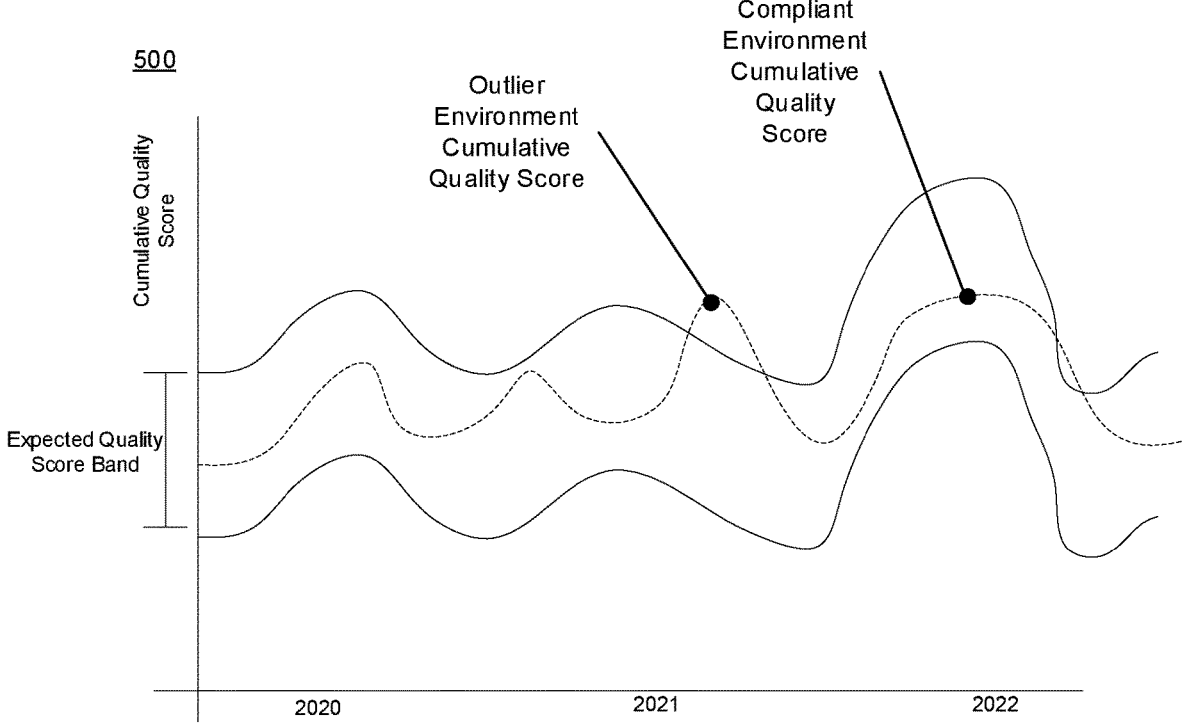
FIG. 5 depicts illustrative graphical user interfaces depicting particle score bands generated in accordance with one or more example embodiments.
Figure 5:
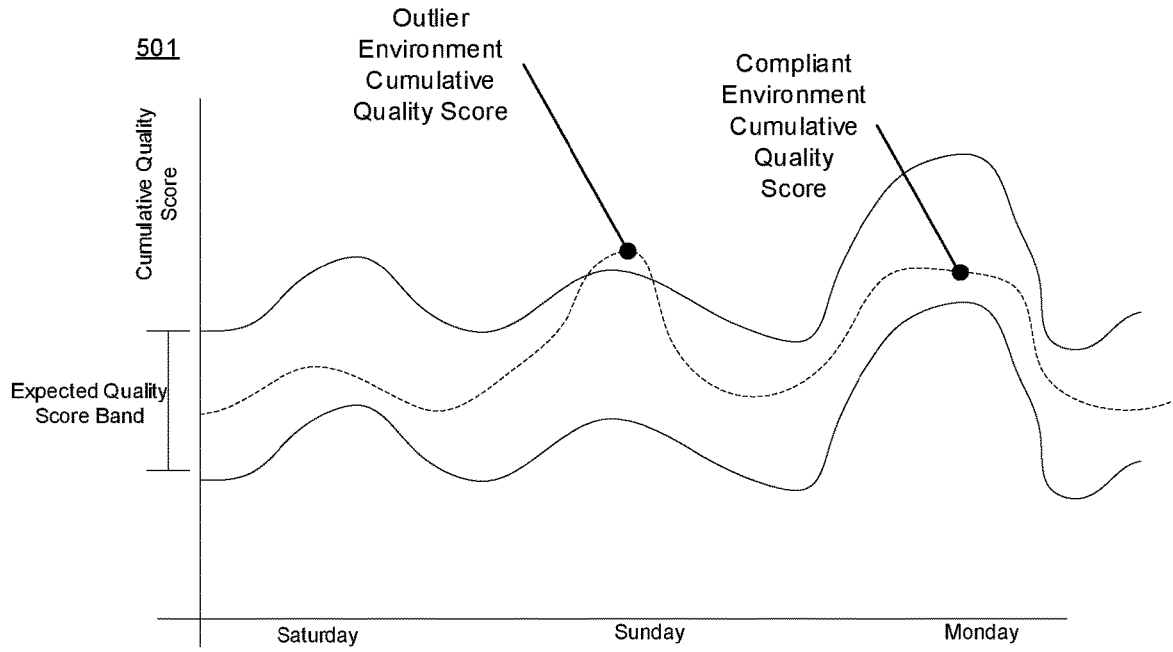

FIG. 5 depicts illustrative graphical user interfaces depicting particle score bands generated during air composition estimation (e.g., 200) using an environment analysis model (e.g., 210). The graphical user interfaces depicting particle score bands may be or include a particle score interface displayed on a user device (e.g., 608). The particle score interface may be displayed based on or in response to receiving one or more commands to display the particle score interface from environment analysis platform 602 (e.g., as described below at step 716). In some instances, the particle score interface may be a graphical user interface similar to annual particle score interface 500. Referring to FIG. 5, in some examples, the annual particle score interface 500 may include information depicting particle score bands. For example, the annual particle score interface 500 may include information such as a lower bound and an upper bound (e.g., solid lines) for an expected particle score band, one or more cumulative particle scores corresponding to particular environments (e.g., dashed line), and a graph plotting the lower bound and the upper bound for the expected particle score band and the one or more cumulative particle scores.

The lower bound and the upper bound for the expected particle score band may be generated by the environment analysis platform 602 during air composition estimation operations based on or in response to the environment analysis platform 602 receiving sets of additional environment information corresponding to an environment (e.g., historical environment information), where each of the sets of additional environment information further corresponds to a specific period of time (e.g., as described below at step 708). In some instances, the expected particle score band may represent a range indicating expected values for a cumulative particle score, where the cumulative particle score is generated by the environment analysis platform 602 (e.g., as described below at step 708) and corresponds to a particular environment. The range indicating the expected values for the cumulative particle score may indicate the expected value at a particular period of time. The one or more cumulative particle scores may indicate a cumulative particle score generated by the environment analysis platform 602 based on a set of environment information and corresponding to a particular environment at a particular time. For example, the one or more cumulative particle scores may indicate the cumulative particle score generated for the particular environment for a particular year (as shown by annual particle score interface 500). The graph plotting the lower bound and the upper bound for the expected particle score band and the one or more cumulative particle scores may include a y-axis representing values of cumulative particle scores and an x-axis representing the periods of time. The graph may further include indicators of the status of a cumulative particle score plotted on the graph, based on the location of the cumulative particle score. For example, the graph may indicate that a cumulative particle score corresponds to a compliant environment where the cumulative particle score is located within the expected particle score band for a particular time period. The graph may indicate that a cumulative particle score corresponds to an outlier environment where the cumulative particle score is located outside the expected particle score band for a particular time period. As shown in the figure, the cumulative particle score may be compliant during certain time periods, and non-compliant during other time periods.

Additionally or alternatively, in some instances, the particle score interface may be a graphical user interface similar to daily particle score interface 501. Referring again to FIG. 5, in some examples, the daily particle score interface 501 may include information depicting particle score bands. For example, daily particle score interface 501 may include information such as a lower bound and an upper bound for an expected particle score band, one or more cumulative particle scores corresponding to particular environments, and a graph plotting the lower bound and the upper bound for the expected particle score band and the one or more cumulative particle scores, in a similar manner to annual particle score interface 500. However, in these examples, the graph plotting the lower bound and the upper bound for the expected particle score band and the one or more cumulative particle scores may include an x-axis representing the periods of time different from the periods of time shown in annual particle score interface 500. For example, daily particle score interface 501 may include an x-axis representing days of the week.

In some examples, additional or alternative particle score interfaces may be displayed that may include x-axes representing different periods of time (e.g., hours, months, seasons, and/or other periods of time). Note that while the particle score interfaces illustrated in FIG. 5 depict a single estimated particle score band in the particle score interface, in some examples the particle score interfaces displayed by the user device may include one or more additional particle score bands generated by the environment analysis platform 602. Additionally, in some examples, the expected quality score band may be based on non-historical information, such as including simple limits of quality scores indicating that the environment does not pose a health risk to humans, other animals, and/or plants.

FIGS. 6A-6B depict an illustrative computing environment for air composition estimation using an environment analysis model in accordance with one or more example embodiments. Referring to FIG. 6A, computing environment 600 may include one or more computer systems. For example, computing environment 600 may include the environment analysis platform 602, an environment information source 604, a cloud storage system 606, and a user device 608.

Environment analysis platform 602 may be a computer system that includes one or more computing devices (e.g., servers, server blades, or the like) and/or other computer components (e.g., processors, memories, communication interfaces) that may be configured to operate, train and/or execute one or more machine learning models, such as environment analysis models. For example, the environment analysis platform 602 may train the one or more environment analysis models to generate estimated air compositions for one or more environments (e.g., as described above and illustrated at FIG. 2B). In some instances, environment analysis platform 602 may be controlled or otherwise maintained by an environment analysis organization such as a financial institution. Although shown as an independent environment analysis platform 602, in some instances, the environment analysis platform 602 may be part of and/or otherwise integrated into the user device 608 without departing from the scope of the disclosure.

Environment information source 604 may be and/or otherwise include one or more computing devices (e.g., servers, server blades, and/or other devices) and/or other computer components (e.g., processors, memories, communication interfaces) that may be configured to gather environment information corresponding to a particular environment and send the environment information to the environment analysis platform 602. Although shown as an independent information source, in some instances, the environment information source 604 may be or include one or more information sources, such as sensors 101, environment information sources 202, sensor 301, and/or sensor 401. The environment information source 604 may be or include one or more of: a particle sensor, a network of sensors located at different geographical locations, a repository of information gathered by multiple unassociated sensors, satellites gathering environmental information, a repository of automotive traffic information, one or more devices gathering environment information of the interior of a building, one or more devices gathering environment information from a moving vehicle, one or more anemometers, a database corresponding to an environment analysis organization, and/or other information sources.

Cloud storage system 606 may be and/or otherwise include one or more computing devices (e.g., servers, server blades, and/or other devices) and/or other computer components (e.g., processors, memories, communication interfaces) that may be configured to create, host, modify, and/or otherwise validate a cloud-based storage system (e.g., a distributed ledger). The cloud storage system 606 may be synchronized across multiple nodes (e.g., sites, institutions, geographical locations, and/or other nodes) and may be accessible by multiple users (who may, e.g., be employees or clients of an environment analysis organization). The data stored at the databases of cloud storage system 606 may include any of the data (e.g., environment information, and/or other information) stored at and/or created by environment analysis platform 602 and/or any additional data. In some instances, the databases stored on cloud storage system 606 may be accessed by, validated by, and/or modified by any of, user device 608, environment analysis platform 602, and/or other devices.

User device 608 may be a computing device (e.g., laptop computer, desktop computer, mobile device, tablet, smartphone, server, server blade, and/or other device) and/or other data storing or computing component (e.g., processors, memories, communication interfaces, databases) that may be configured to transfer data between users and/or perform other user functions (e.g., receiving display commands, and/or other functions). In one or more instances, user device 608 may correspond to a user account (which may, e.g., be associated with an employee of the environment analysis organization, may be a client of the environment analysis organization, may be otherwise associated with the enterprise organization, or the like). In one or more instances, the user device 608 may be configured to communicate with one or more systems (e.g., environment analysis platform 602, environment information source 604, and/or other systems) to perform a data transfer, receive display commands, and/or to perform other functions.

Computing environment 600 also may include one or more networks, which may interconnect environment analysis platform 602, environment information source 604, cloud storage system 606, user device 608. For example, computing environment 600 may include a network 601 (which may interconnect, e.g., environment analysis platform 602, environment information source 604, cloud storage system 606, and user device 608).

In one or more arrangements, environment analysis platform 602, environment information source 604, cloud storage system 606, user device 608 may be any type of computing device capable of sending and/or receiving requests and processing the requests accordingly. For example, environment analysis platform 602, environment information source 604, cloud storage system 606, user device 608, and/or the other systems included in computing environment 600 may, in some instances, be and/or include server computers, desktop computers, laptop computers, tablet computers, smart phones, or the like that may include one or more processors, memories, communication interfaces, storage devices, and/or other components. As noted above, and as illustrated in greater detail below, any and/or all of environment analysis platform 602, environment information source 604, cloud storage system 606, user device 608, may, in some instances, be special-purpose computing devices configured to perform specific functions. For example, each may include memory that includes computer readable instructions that, when executed by a processor, cause the special-purpose computing device to perform one or more functions described herein.

Referring to FIG. 6B, environment analysis platform 602 may include one or more processors 609, memory 610, and communication interface 611. A data bus may interconnect processor 609, memory 610, and communication interface 611. Communication interface 611 may be a network interface configured to support communication between environment analysis platform 602 and one or more networks (e.g., network 601, or the like). Communication interface 611 may be communicatively coupled to the processor 609. Communication interface 611 may be configured to receive sets of environment information from one or more environment information sources via one or more wireless data connections. Memory 610 may include one or more program modules having instructions that, when executed by processor 609, cause environment analysis platform 602 to perform one or more functions described herein and/or one or more databases that may store and/or otherwise maintain information which may be used by such program modules and/or processor 609. In some instances, the one or more program modules and/or databases may be stored by and/or maintained in different memory units of environment analysis platform 602 and/or by different computing devices that may form and/or otherwise make up environment analysis platform 602. For example, memory 610 may have, host, store, and/or include environment analysis module 610*a*, environment analysis database 610*b*, and machine learning engine 610*c*.

Environment analysis module 610*a* may have instructions that direct and/or environment analysis platform 602 to perform environment analysis (e.g., as described with respect to FIG. 2A). Environment analysis database 610*b* may have instructions causing environment analysis platform 602 to store environment information, estimated air compositions, and/or cumulative particle scores (that may, e.g., be used to perform environment analysis). Machine learning engine 610*c* may contain or include instructions causing environment analysis platform 602 to train, implement, and/or update an environment analysis model (e.g., as described with respect to FIG. 2B). In some instances, machine learning engine 610*c* may be used by environment analysis platform 602 and/or environment analysis module 610*a* to refine and/or otherwise update methods for environment analysis, and/or other methods described herein.

Figure 7:
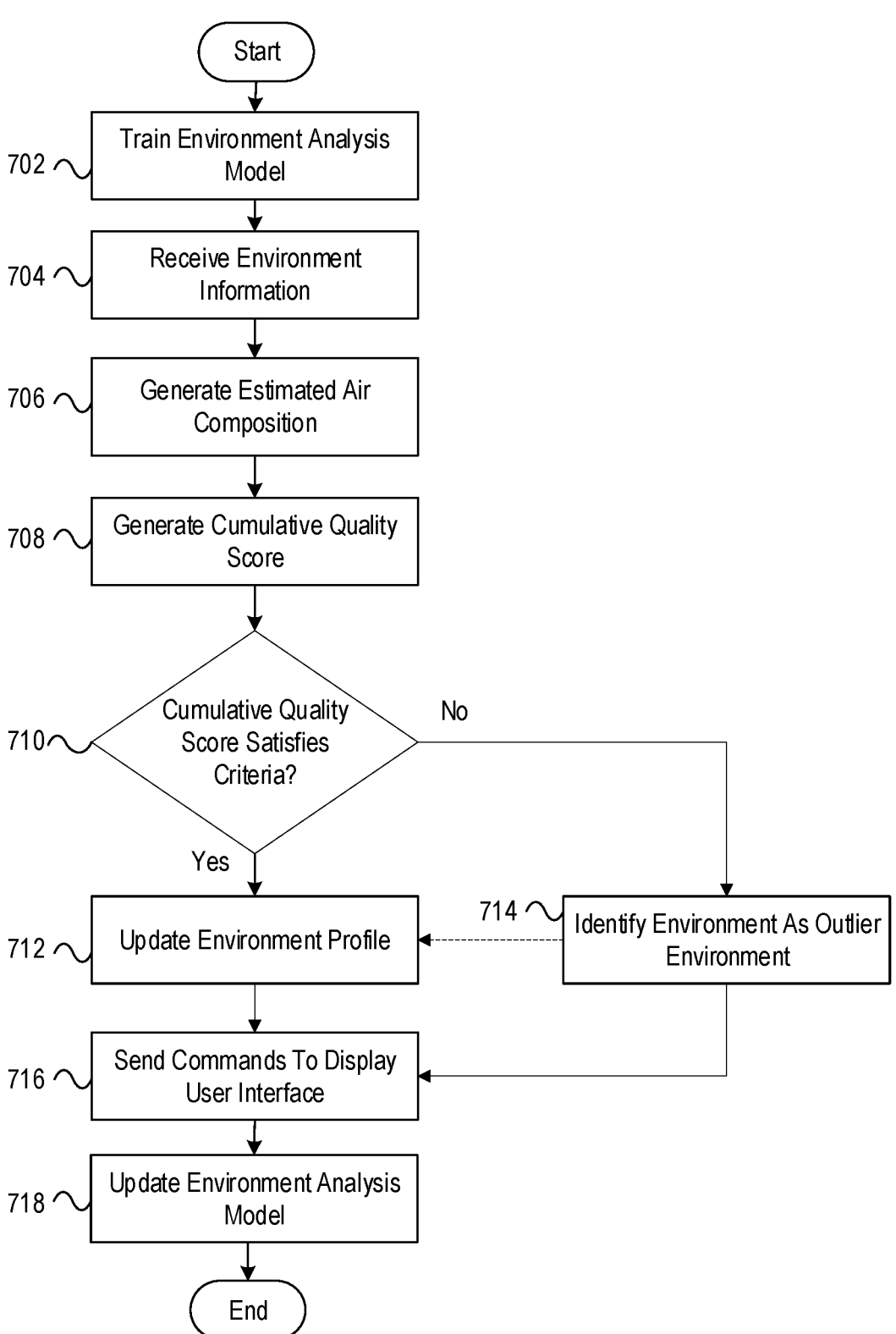
FIG. 7 depicts an illustrative method for air composition estimation in accordance with one or more example embodiments.

FIG. 7 depicts an illustrative method for air composition estimation using an environment analysis model in accordance with one or more example embodiments. Referring to FIG. 7, at step 702, the environment analysis platform 602 may train the environment analysis model. In training the environment analysis model, the environment analysis platform 602 may configure and/or otherwise train the environment analysis model to generate an estimated air composition based on environment information. For example, the environment analysis platform 602 may configure and/or otherwise train the environment analysis model using the methods illustrated in FIG. 2B described above in environment analysis model training 209, and/or other training methods.

At step 704, the environment analysis platform 602 may receive environment information. For example, the environment analysis platform 602 may receive the environment information in the form of a set of environment information from the environment information source 604. The environment analysis platform 602 may receive the set of environment information via a wired or wireless data connection established between the environment information source 604 and the communication interface 611. In some instances, the environment analysis platform 602 may additionally or alternatively receive the set of environment information indirectly. For instance, the environment analysis platform 602 may receive the set of environment information from a repository (e.g., a web-based server, database, cloud storage system, and/or other repositories), which may for example be implemented in cloud storage system 606. In these examples, the environment analysis platform 602 may retrieve the set of environment information from the repository (e.g., via webscraping methods, application programming interface (API) calls, information transfer requests, and/or other methods).

The set of environment information may include one or more measured variables corresponding to one or more known attributes of a known particle, and/or one or more additional environment variables. The one or more additional environment variables may include one or more of: wind speed, wind direction, particle concentrations, gas concentrations, temperature information, relative humidity information, air pressure information, dew point information, vibration information, noise information, environment ventilation status, altitude information, topographical information, occupancy information, traffic counts, mold growth information, mildew growth information, population information, luminosity information, precipitation information, and/or virus detection information. In some instances, the environment analysis platform 602 may receive additional sets of environment information from the environment information source 604. In these instances, each of the sets of additional environment information may correspond to a specific period of time. For example, the environment analysis platform 602 may receive a set of environment information corresponding to Monday, a set of information corresponding to Tuesday, a set of information corresponding to a specific week of the year, a set of information corresponding to a specific month, and so on.

At step 706, the environment analysis platform 602 may generate, using the environment analysis model, the estimated air composition for the environment. In generating the estimated air composition, the environment analysis platform 602 may input the set of environment information into the environment analysis model. The environment analysis model may use the set of environment information to estimate one or more types of particle present in the environment (e.g., one or more gas molecules (e.g., carbon dioxide molecules, carbon monoxide molecules, and/or other gas molecules), one or more particulates (e.g., aerosol particles, soot, tobacco smoke, smog, oil smoke, fly ash, and/or other particulates), one or more types of dust (e.g., cement dust, atmospheric dust, heavy dust, and/or other types of dust), one or more biological contaminants (e.g., pollen, mold spores, mildew spores, bacteria, viruses, and/or other biological contaminations) and/or other types of particle). In some instances, the estimated air composition may be based wholly or in part on one or more particle sizes (e.g., measured by sensor 101 or 301) included in the set of environment information. For example, inputting a specific particle size may cause the environment analysis model to generate an estimated air composition identifying a type of particle corresponding to the specific particle size. Additionally or alternatively, the estimated air composition may be based wholly or in part on one or more particle counts (e.g., measured by sensor 101 or 301) included in the set of environment information. For example, inputting a specific particle count may cause the environment analysis model to generate an estimated air composition identifying a type of particle corresponding to the specific particle count (e.g., based on a stored correlation between the specific particle count and historical estimated air compositions). Additionally or alternatively, in some examples, other environment variables may be used to generate the estimated air composition. In some examples, the environment analysis model may associate a particular particle size and/or particle count with different types of particles, depending upon the additional environment variables (e.g. temperature, humidity, season, time of day, etc.). In some instances, estimated air composition may be based wholly or in part on one or more variables. For example, inputting a current air pressure, current relative humidity, current wind speed/direction, and/or other current variables may cause the environment analysis model to generate an estimated air composition identifying a type of particle corresponding to one or more current variables of the additional environment variables. For instance, based on a stored correlation between a current humidity and historical information (e.g., historical particle counts, historical particles sizes, historical humidity, etc. (which may, e.g., have previously been used to train the environment analysis model), the environment analysis model may generate an estimated air composition identifying at least one particle type associated with the historical humidity. The estimated air composition may be or include one or more identified types of particles and corresponding particle counts.

In some examples, the environment analysis platform 602 may have previously trained the environment analysis model to employ an environment analysis algorithm to determine the estimated air composition. In some instances, the environment analysis algorithm may use some or all of the information included in the set of environment information.

In using the environment analysis algorithm, the environment analysis platform 602 may use some or all of the information in one or more historical sets of environment information to identify currently unidentified particle types from the set of environment information. For example, the environment analysis platform 602 may execute the environment analysis algorithm using the following constraints/parameters:

---

If:
    (Historical Particle 1 size =Unidentified Particle 1 size),
    and
    (Historical Particle 1 vibration frequency = Unidentified
    Particle 1 vibration frequency),
    and
    (Historical air pressure = current air pressure);
then
    Unidentified Particle 1 = Historical Particle 1.

---

In this example, based on identifying that unidentified particle 1 is equivalent to historical particle 1, then the environment analysis platform 602 may generate an estimated air composition including historical particle 1. Here, "equivalent" was formulated to consider size, and vibration frequency at a common air pressure, but different or additional variables could be included in the determination. Additionally or alternatively, the environment analysis platform 602 may execute the environment analysis algorithm using one or more additional constrains/parameters, which may, e.g., include one or more additional environment variables.

In some instances, after generating the estimated air composition, the environment analysis platform 602 may configure an environment profile corresponding to the environment. For example, the environment analysis platform 602 may configure the environment profile to maintain a record of the environment. The record of the environment may be or include geographic information of the environment (e.g., a geographic location, topography, and/or other geographic information), the estimated air composition of the environment, one or more historical estimated air compositions of the environment, an environmental status of the environment (e.g., an indicator of whether the environment is a compliant environment or an outlier environment), and/or other information. The environment analysis platform 602 may maintain the record by storing the environment profile at a storage system, for example in internal memory of the environment analysis platform 602, and/or in an external memory, such as cloud storage system 606.

At step 708, the environment analysis platform 602 may generate a cumulative particle score based on the estimated air composition. In generating the cumulative particle score, the environment analysis platform 602 may generate the cumulative particle score as an integer value, alphanumeric character, percentage value, decimal value, hexadecimal value, binary value, and/or other representations of the cumulative particle score. The cumulative particle score may indicate a measure of air quality in the environment corresponding to the set of environment information. For example, a first environment corresponding to a higher cumulative particle score than a second environment may contain a higher concentration of particles than the second environment. In generating the cumulative particle score, the environment analysis platform 602 may analyze the particle types and corresponding particle counts included in the estimated air composition. For example, in some instances the environment analysis platform 602 may generate a cumulative particle score equivalent to the sum of the particle counts corresponding to each particle type. In another example, in generating the cumulative particle score, the environment analysis platform 602 may assign weight coefficients to specific particle types (e.g., indicating more harmful or more benign particles). The environment analysis platform 602 may analyze estimated air composition to determine the identified particle types and the corresponding particle counts. The environment analysis platform 602 may multiply the particle counts corresponding to each specific identified particle type by the respective assigned weight coefficient to generate weighted values. The environment analysis platform 602 may compute the cumulative particle score by calculating the sum of the weighted values. For example, the environment analysis platform 602 may calculate the cumulative particle score by executing the following formula:

$$\begin{aligned} \text{Cumulative Quality Score} = \\ (\text{Particle A Coefficient} * \text{Particle A Count}) + \\ (\text{Particle B Coefficient} * \text{Particle B Count}) + \\ (\text{Particle C Coefficient} * \text{Particle C Count}). \end{aligned}$$

In some instances, the environment analysis platform 602 may automatically assign the weight coefficients based on predetermined settings. For example, the environment analysis platform 602 may include predetermined settings assigning weight coefficients based on a consideration of danger of the particle types (e.g., particle types known to damage human lungs may be assigned higher weight coefficients than particle types that are not harmful to human lungs, and/or other considerations of danger). In some examples, the environment analysis platform 602 may additionally or alternatively assign the weight coefficients based on user input (e.g., user input received from an employee of an environment analysis organization, and/or other individuals).

In some examples, the environment analysis platform 602 may additionally have received sets of additional environment information from the environment information source 604 (e.g., as described above at step 704). Each of the sets of additional environment information may correspond to a specific period of time (e.g., a specific day of the week, and/or other periods of time). In some instances, one or more of the sets of additional environment information may correspond to the same environment as the set of environment information received at step 704. Additionally or alternatively, one or more of the sets of additional environment information may correspond to a different environment that may, e.g., possess similar characteristics (e.g., humidity level, air pressure, climate, and/or other characteristics) to the environment corresponding to the set of environment information.

Based on the sets of additional environment information and the set of environment information, the environment analysis platform 602 may generate one or more expected particle score bands for a particular environment. In generating the one or more expected particle score bands, the environment analysis platform 602 may analyze the sets of additional environment information and the set of environment information to determine an upper bound and a lower bound for each of the one or more expected particle score bands. For example, the environment analysis platform 602 may have received five sets of additional environment information, where the five sets of additional environment information each correspond to one of the previous five Fridays. In this example, based on the five sets of additional environment information, the environment analysis platform 602 may determine a maximum and a minimum cumulative particle score for the previous five Fridays (e.g., by using the environment analysis model to generate estimated air compositions and generating corresponding cumulative particle scores, as described above at steps 706-708). The environment analysis platform 602 may use the maximum and minimum cumulative particle scores as the upper bound and lower bound of the expected particle score band, respectively. Although the above example describes generating a cumulative particle score band for a specific day of the week, in some examples the environment analysis platform 602 may generate one or more cumulative particle score bands corresponding to different periods of time (e.g., months, weeks, years, seasons, and/or other periods of time) and/or generate one or more cumulative particle score bands corresponding to multiple specific periods of time (e.g., each day of the week, each month of the year, each season of the year, and/or other specific periods of time).

In some instances, the one or more expected particle score bands may represent ranges indicating expected values for a cumulative particle score corresponding to a particular environment. In some examples, the environment analysis platform 602 may plot the one or more expected quality score bands on a graph that may, e.g., be displayed to a user via a graphical user interface (e.g., as illustrated at FIG. 5 and described above).

At step 710, the environment analysis platform 602 may determine whether or not the cumulative particle score satisfies a criteria. The criteria may be or include a threshold value, a threshold range, a limit on the particle count of one or more particle types, and/or other criteria. The criteria may indicate whether the environment is a compliant environment or an outlier environment. In determining whether or not the cumulative particle score satisfies the criteria, the environment analysis platform 602 may compare the cumulative quality score to the criteria. For example, the cumulative quality score may have or be a numerical value of 140, and the criteria may have or be a threshold value of 100, where cumulative particle scores below the threshold value satisfy the criteria. Based on the comparison, the environment analysis platform 602 may determine that the cumulative quality score exceeds the threshold value and thus fails to satisfy the criteria, which may, e.g., indicate that the corresponding environment is an outlier environment.

In another instance, the cumulative quality score may be or include a sum of particle counts corresponding to specific particle types, and the criteria may be a limit on a particle count corresponding to a specific particle, where particle counts corresponding to the specific particle and exceeding the limit fail to satisfy the criteria. In this instance, a cumulative quality score including a particle count of 50 micrograms per cubic meter of Particle Type A would fail to satisfy a criteria imposing a limit of 35 micrograms per cubic meter on Particle Type A. In another example, the criteria may be or include one or more expected particle score bands (e.g., the one or more expected particle score bands generated and described above at step 708). In determining whether the cumulative particle score satisfies the criteria, the environment analysis platform 602 may determine whether or not the cumulative particle score is within the one or more expected particle score bands. For example, a cumulative particle score corresponding to a specific period of time, that is or includes a value outside of the expected quality score band corresponding to the specific period of time, may fail to satisfy the criteria.

Based on or in response to determining that the cumulative particle score satisfies the criteria, the environment analysis platform 602 may proceed to update the environment profile (e.g., as described below at step 712). Based on or in response to determining that the cumulative particle score fails to satisfy the criteria, the environment analysis platform 602 may instead identify the environment corresponding to the cumulative particle score as an outlier environment (e.g., as described below at step 714).

At step 712, based on or in response to determining that the cumulative particle score satisfies the criteria, the environment analysis platform 602 may proceed to update the environment profile (e.g., the environment profile configured at step 706, as described above). In updating the environment profile, the environment analysis platform 602 may modify or confirm the environment status of the environment based on the determination. For example, if the environment profile includes an environment status indicating that the environment is a compliant environment, the environment analysis platform 602 may confirm the environment status. If the environment profile includes an environment status indicating that the environment is an outlier environment, the environment analysis platform 602 may modify the environment status to indicate that the environment is now a compliant environment. Based on or in response to updating the environment profile, the environment analysis platform 602 may proceed to send one or more commands to display a user interface (e.g., as described below at step 716).

At step 714, based on or in response to determining that the cumulative particle score fails to satisfy the criteria, the environment analysis platform 602 may identify the environment corresponding to the cumulative particle score as an outlier environment. Based on or in response to identifying the environment as an outlier environment, the environment analysis platform 602 may generate one or more hazard notifications. The hazard notifications may indicate the cumulative particle score's failure to satisfy the criteria and the estimated air composition in order to alert individuals or organizations of a potential environmental hazard located in the environment. In some instances, based on identifying the environment as an outlier environment, the environment analysis platform 602 may additionally update the environment profile (e.g., via step 712). In updating the environment profile, the environment analysis platform 602 may modify or confirm the environment status of the environment based on the determination. For example, if the environment profile includes an environment status indicating that the environment is an outlier environment, the environment analysis platform 602 may confirm the environment status. If the environment profile includes an environment status indicating that the environment is a compliant environment, the environment analysis platform 602 may modify the environment status to indicate that the environment is now an outlier environment. Based on or in response to identifying the environment as an outlier environment, the environment analysis platform 602 may proceed to send one or more commands to display a user interface (e.g., as described below at step 716).

Figure 8A:
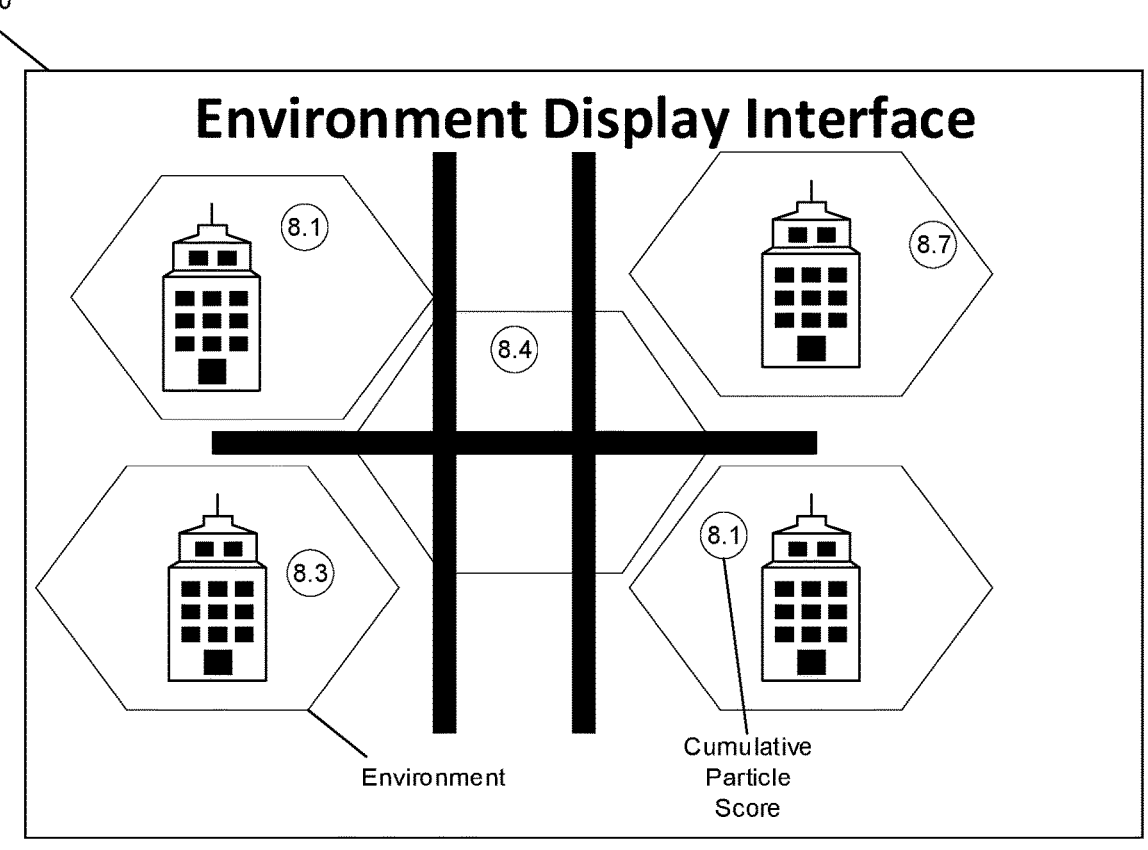
FIGS. 8A-8C depict illustrative graphical user interfaces depicting air composition estimation in accordance with one or more example embodiments.

At step 716, the environment analysis platform 602 may send one or more commands to display a user interface to user device 608. For example, the environment analysis platform 602 may send the one or more commands to user device 608 via the communication interface 611 while a wired or wireless data connection is established. The one or more commands to display the user interface may cause user device 608 to display the user interface. For example, in the user device 608 may display an environment display interface. In displaying an environment display interface, the user device 608 may display a graphical user interface similar to environment display interface 800, which is illustrated in FIG. 8A. Referring to FIG. 8A, in some instances, the environment display interface 800 may include information corresponding to the environment and the environment analysis operations performed by the environment analysis platform 602. For example, the environment display interface 800 may include information such as a map of a geographical region (e.g., a city grid map, a three-dimensional city map, and/or other geographical maps), one or more environments the environment analysis platform 602 has performed environment analysis operations on, one or more cumulative particle scores corresponding to the one or more environments, and/or other information.

Figure 8B:
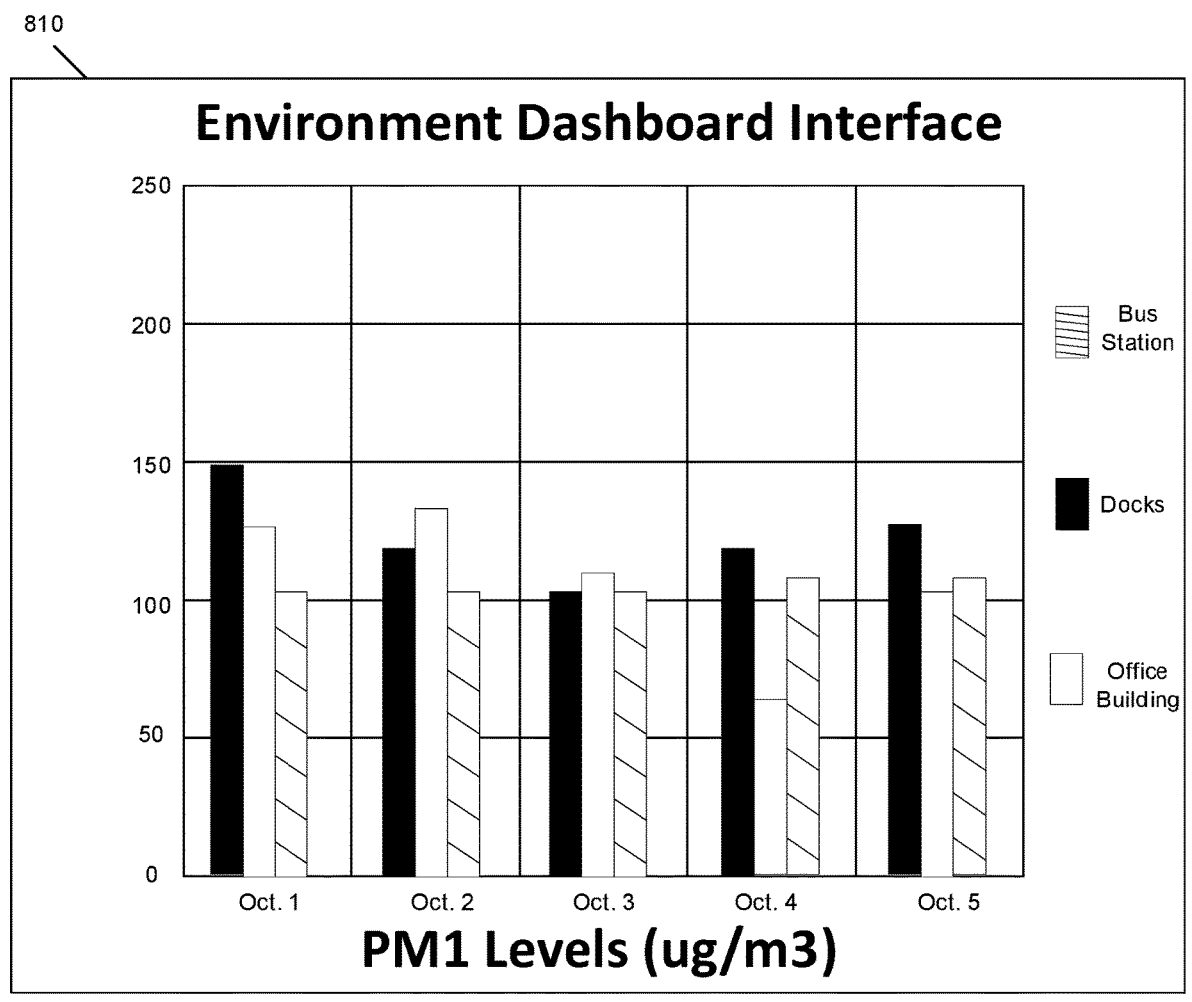

Additionally or alternatively, based on or in response to the one or more commands to display the user interface, the user device 608 may display an environment dashboard interface. For example, in displaying the environment dashboard interface, the user device 608 may display a graphical user interface similar to environment dashboard interface 810, which is illustrated in FIG. 8B. The environment dashboard interface 810 may correspond to the environment. Referring to FIG. 8B, in some instances, the environment dashboard interface 810 may include information corresponding to environment. For example, the environment dashboard interface 810 may include information such as a representation based on the estimated air composition corresponding to the environment, and/or other information. For example, the representation may be or include a graph, which may, e.g., display the particle counts for one or more particle types identified by the environment analysis platform 602 and included in the estimated air composition. In these examples, the graph may display the particle counts over a period of time (e.g., days, weeks, months, and/or other periods of time).

Additionally or alternatively, based on or in response to the one or more commands to display the user interface, the user device 608 may display a particle score interface. For example, in displaying the particle score interface, the user device 608 may display a graphical user interface similar to annual particle score interface 500 and/or daily particle score interface 501, which are illustrated in FIG. 5. The user device 608 may display the particle score interface as illustrated in FIG. 5 and described above.

Figure 8C:
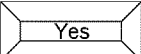
Figure 8C:
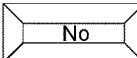

In some instances, based on the determination of whether or not the cumulative particle score satisfies the criteria (e.g., as described above at step 710), the environment analysis platform 602 may send one or more commands to display a user interface indicating a result of the determination to user device 608. Based on or in response to the one or more commands to display the user interface, the user device 608 may display an environmental hazard notification interface. In some instances, the environmental hazard notification interface may be configured to receive user input through the user device 608. For example, in displaying the environmental hazard notification interface, the user device 608 may display a graphical user interface similar to environmental hazard notification interface 820, which is illustrated in FIG. 8C. Referring to FIG. 8C, the environmental hazard notification interface 820 may include information corresponding to the determination. For example, the environmental hazard notification interface 820 may include information such as an alert indicating the status of the environment (e.g., a compliant environment, an outlier environment, and/or other statuses), one or more locations of the environment information source (e.g., environment information source 604) that provided sets of environment information (e.g., the set of environment information), and one or more descriptions of the determination (e.g., a description of the criteria and why the cumulative particle score failed to satisfy the criteria, and/or other descriptions). In some instances, based on a determination that the cumulative particle score fails to satisfy the criteria, the environmental hazard notification interface 820 may additionally or alternatively include one or more hazard notifications (e.g., the hazard notifications generated at step 714, as described above).

The environmental hazard notification interface 820 may also display input mechanisms or selectable options requesting user input. For example, the environmental hazard notification interface 820 may display one or more of: a button or buttons, toggle or toggles, check box or boxes, and/or other interface elements. For example, as illustrated in FIG. 8C, the input mechanisms may be buttons the user can select to decide whether or not to alert additional devices. In some instances, based on user input directing the user device 608 to alert additional devices, the user device 608 may send one or more commands directing the environment analysis platform 602 to alert additional devices. In these instances, the one or more commands directing the environment analysis platform 602 to alert additional devices may cause the environment analysis platform 602 to send an environmental hazard notification interface to one or more additional user devices (e.g., one or more environment information sources (such as environment information source 604), devices corresponding to clients of an environment analysis organization, devices corresponding to employees of an environment analysis organization, devices corresponding to employees of an environmental alert service, and/or the like).

For example, in some instances the environment information source 604 may be or include one or more non-static devices (e.g., mobile communication devices, wearable devices, and/or other devices). In these instances, based on user input directing the environment analysis platform 602 to alert additional devices, the environment analysis platform 602 may send an environmental hazard notification interface to the one or more non-static devices. In some instances, the one or more non-static devices may notify the user of the environmental hazard notification interface. For example, the one or more non-static devices may be or include a wearable device (e.g., a band, smart watch, smart clothing, smart bracelet, fitness tracker, smart belt, and/or other wearable devices) configured to produce a haptic response (e.g., a vibration, buzz, pulse, and/or other haptic responses) based on receiving the environmental hazard notification interface.

In some instances, in alerting the additional devices, the environment analysis platform 602 may alert list of mobile devices corresponding to a specific geographic location. The environment analysis platform 602 may have previously received a list of all the mobile devices present in the specific geographic location and configured to receive an environmental hazard notification interface. For example, the environment analysis platform 602 may have received a list of mobile devices corresponding to users who subscribe to a service provided by an environment analysis organization managing the environment analysis platform 602, and/or other lists. The environment analysis platform 602 may have received the list via the communication interface 611 and while a wireless data connection was established. The environment analysis platform 602 may send one or more commands directing each mobile device of the list of mobile devices corresponding to the specific geographic location to display a user interface (e.g., an environmental hazard notification interface, and/or other interfaces). In some instances, the specific geographic location may be a configurable location configured by the user of the environment analysis platform 602. For example, a user (e.g., an employee of an environment analysis organization, and/or other users) may configure the specific geographic location to encompass one or more environments on which the environment analysis platform 602 performs environment analysis operations.

Referring back to FIG. 7, at step 718, the environment analysis platform 602 may update the environment analysis model. In updating the environment analysis model, the environment analysis platform 602 may refine and/or otherwise update the environment analysis model to improve the accuracy in generating an estimated air composition based on environment information. For example, the environment analysis platform 602 may refine and/or otherwise update the environment analysis model as described above with respect to FIG. 2B with environment analysis model training 209, and/or other updating methods.

The environment analysis platform 602 may perform additional environment analysis operations to those included in the method illustrated in FIG. 7 and described above. In some instances, the environment analysis platform 602 may determine an age of environment information source 604 (which may, e.g., be a particle sensor, and/or other source of environment information) based on the set of environment information. In determining the age of the environment information source 604, the environment analysis platform 602 may compare the set of environment information gathered by the environment information source 604 to one or more historical sets environment information and/or known environment information. For example, the environment analysis platform 602 may determine that a particle count included in the set of environment information differs from a particle count included in one or more historical sets of environment information corresponding to the same environment by a specific amount. Based on a determination that the particle count included in the set of environment information should match the particle count included in the one or more historical sets of environment information (e.g., by analyzing the particle count included in current known environment information, which may have been gathered by a different environment information source), the environment analysis platform 602 may identify that the accuracy of environment information source 604 has degraded to or below a particular accuracy threshold. The environment analysis platform 602 may determine the age of the environment information source 604 by comparing the particular accuracy threshold to a list of accuracy thresholds corresponding to specific ages of environment information sources.

In some instances, based on determining the age of the environment information source 604, the environment analysis platform 602 may cause the environment information source 604 to recalibrate in order to improve the accuracy of environment information source 604. For example, the environment analysis platform 602 may send a notification to a user (e.g., an employee of an environment analysis organization managing environment information source 604, and/or other users) directing the user to recalibrate environment information source 604.

In performing additional environment analysis operations, the environment analysis platform 602 may additionally or alternatively determine a source of one or more particles identified in the estimated air composition. In some instances, the environment analysis platform 602 may determine the source of the one or more particles concurrent with and/or after generating the estimated air composition (e.g., as described at step 706 above). In identifying the source of the one or more particles, the environment analysis platform 602 may analyze a subset of the set of environment information in order to determine a source location corresponding to the source of the one or more particles identified in the estimated air composition. The environment analysis platform 602 may analyze the particle size, particle weight, particle movement information (e.g., movement direction, movement speed, and/or other movement information), wind speed, wind direction, and/or other environment information. For example, the environment analysis platform 602 may compare the specific particle size, specific particle weight, and specific particle movement speed of a specific particle with the wind speed and wind direction and determine, based on the comparison a source location from which a particle corresponding to the specific particle size, specific particle weight, and specific particle movement speed could have traveled based on the wind speed and wind direction.

Based on determining the source location, the environment analysis platform 602 may determine the source of the one or more particles based on geographic information. The geographic information may be retrieved from cloud storage system 606 and/or other information storage systems. In determining the source of the one or more particles based on geographic information, the environment analysis platform 602 may compare the source location with the geographic information. For example, based on geographic information indicating the presence of a particular structure (e.g., a power plant, refinery, and/or other structure) at or near the source location, the environment analysis platform 602 may identify the particular structure as the source of the one or more particles identified in the estimated air composition.

Based on determining the source of the one or more particles identified in the estimated air composition, the environment analysis platform 602 may update the estimated air composition generated at step 706. In updating the estimated air composition, the environment analysis platform 602 may update (e.g. by identifying, reclassifying, and/or otherwise updating) one or more identified particle types included in the estimated air composition. For example, based on determining the source of the one or more particles identified in the estimated air composition to be a particular structure (e.g., a power plant, refinery, and/or other structure), the environment analysis platform 602 may reclassify one or more identified particle types as a different particle type associated with the particular structure.

Additionally or alternatively, in performing additional environment analysis operations, the environment analysis platform 602 may cause, based on the determination of whether or not the cumulative particle score satisfies the criteria (e.g., as described at step 710 above) one or more environment safety actions to occur. For example, in some instances the environment analysis platform 602 may be deployed as part of a system (e.g., an environment control system, and/or other systems). In these instances, the environment analysis platform 602 may cause the activation of one or more additional devices within the system. For example, the environment analysis platform 602 may cause the activation of an air filtration device which may, e.g., be deployed and/or otherwise installed in the same location as the environment information source 604. The environment analysis platform 602 may cause the activation of the one or more additional devices within the system by sending one or more commands (e.g., via the communication interface 611) to the one or more additional devices within the system.

One or more aspects of the disclosure may be embodied in computer-usable data or computer-executable instructions, such as in one or more program modules, executed by one or more computers or other devices to perform the operations described herein. Generally, program modules include routines, programs, objects, components, data structures, and the like that perform particular tasks or implement particular abstract data types when executed by one or more processors in a computer or other data processing device. The computer-executable instructions may be stored as computer-readable instructions on a computer-readable medium such as a hard disk, optical disk, removable storage media, solid-state memory, RAM, and the like. The functionality of the program modules may be combined or distributed as desired in various embodiments. In addition, the functionality may be embodied in whole or in part in firmware or hardware equivalents, such as integrated circuits, application-specific integrated circuits (ASICs), field programmable gate arrays (FPGA), and the like. Particular data structures may be used to more effectively implement one or more aspects of the disclosure, and such data structures are contemplated to be within the scope of computer executable instructions and computer-usable data described herein.

As described herein, the various methods and acts may be operative across one or more computing servers and one or more networks. The functionality may be distributed in any manner, or may be located in a single computing device (e.g., a server, a client computer, and the like). For example, in alternative embodiments, one or more of the computing platforms discussed above may be combined into a single computing platform, and the various functions of each computing platform may be performed by the single computing platform. In such arrangements, any and/or all of the above-discussed communications between computing platforms may correspond to data being accessed, moved, modified, updated, and/or otherwise used by the single computing platform. Additionally or alternatively, one or more of the computing platforms discussed above may be implemented in one or more virtual machines that are provided by one or more physical computing devices. In such arrangements, the various functions of each computing platform may be performed by the one or more virtual machines, and any and/or all of the above-discussed communications between computing platforms may correspond to data being accessed, moved, modified, updated, and/or otherwise used by the one or more virtual machines.

Aspects of the disclosure have been described in terms of illustrative embodiments thereof. Numerous other embodiments, modifications, and variations within the scope and spirit of the appended claims will occur to persons of ordinary skill in the art from a review of this disclosure. For example, one or more of the steps depicted in the illustrative figures may be performed in other than the recited order, and one or more depicted steps may be optional in accordance with aspects of the disclosure.

What is claimed is:

1. A computing platform comprising:
   at least one processor;
   a communication interface communicatively coupled to the at least one processor; and
   memory storing computer-readable instructions that, when executed by the at least one processor, cause the computing platform to:

train, based on historical sets of environment information, and known air compositions, an environment analysis model, wherein the training of the environment analysis model configures the environment analysis model to output estimated air compositions;

receive, via the communication interface from one or more environment information sources, a set of environment information corresponding to an environment, wherein the set of environment information comprises:

one or more measured variables corresponding to one or more attributes of a known particle, and one or more additional environment variables;

provide the one or more measured variables and the one or more additional environment variables as input to the environment analysis model, to generate an estimated air composition;

generate, based on the estimated air composition, a cumulative particle score;

determine whether or not the cumulative particle score satisfies a criteria, wherein the criteria indicates whether the environment is a compliant environment or an outlier environment; and send, based on the determination, one or more commands directing a user device to display a user interface, wherein the user interface comprises a notification indicating a result of the determination.

2. The computing platform of claim 1, wherein the estimated air composition identifies, based on the one or more additional environment variables, one of two or more different particle types corresponding to the same one of the one or more attributes of the known particle.

3. The computing platform of claim 1, wherein the one or more additional environment variables comprise one or more of:

wind speed, wind direction, particle concentration, gas concentration, temperature, relative humidity, air pressure, dew point, vibration frequency, noise level, ventilation status, altitude, topographical information, occupancy, traffic counts, mold growth information, mildew growth information, population information, luminosity information, precipitation information, or virus detection information.

4. The computing platform of claim 1, wherein the one or more attributes of the known particle comprise a measurable attribute of a particle in the environment, including:

particle size, particle count, particle concentration, particle vibration frequency, or particle movement speed.

5. The computing platform of claim 1, wherein the estimated air composition comprises one or more particle types, wherein each of the one or more particle types corresponds to one of the one or more attributes.

6. The computing platform of claim 1, wherein the memory stores additional computer-readable instructions that, when executed by the at least one processor, cause the computing platform to:

receive, from the one or more environment information sources, sets of additional environment information corresponding to the environment, wherein each of the sets of additional environment information further corresponds to a specific period of time;

generate, based on the sets of additional environment information and the set of environment information, one or more expected particle score bands corresponding to one or more additional periods of time; and cause, based on one or more commands directing the user device to display a particle score interface, wherein the particle score interface comprises the one or more expected particle score bands and the cumulative particle score.

7. The computing platform of claim 6, wherein determining whether or not the cumulative particle score satisfies the criteria comprises determining whether or not the cumulative particle score is within the one or more expected particle score bands.

8. The computing platform of claim 1, wherein the one or more additional environment variables comprise information indicating compositions of particles.

9. The computing platform of claim 1, wherein the one or more environment information sources comprise one or more non-static devices, and wherein the memory stores additional computer-readable instructions that, when executed by the at least one processor, cause the computing platform to:

send, to the one or more non-static devices, one or more additional commands directing the one or more non-static devices to display an additional user interface, wherein the additional user interface comprises an additional notification indicating the result of the determination.

10. The computing platform of claim 9, wherein the one or more non-static devices comprise one or more mobile communication devices or one or more wearable devices.

11. The computing platform of claim 1, wherein the memory stores additional computer-readable instructions that, when executed by the at least one processor, cause the computing platform to: determine a calibration of a particle sensor based on the set of environment information.

12. The computing platform of claim 1, wherein the memory stores additional computer-readable instructions that, when executed by the at least one processor, cause the computing platform to:

determine, based on the set of environment information and using the environment analysis model, a source of one or more particles identified in the estimated air composition; and update, based on the source of the one or more particles identified in the estimated air composition, the estimated air composition.

13. The computing platform of claim 1, wherein the memory stores additional computer-readable instructions that, when executed by the at least one processor, cause the computing platform to:

determine the user device corresponds to a specific geographic location, wherein the sending of the one or more commands is based on the determination that the user device corresponds to the specific geographic location.

14. The computing platform of claim 1, wherein the one or more environment information sources comprise one or more of:

a particle sensor, a network of sensors located at different geographical locations, a repository of information gathered by multiple unassociated sensors, satellites gathering environmental information, a repository of automotive traffic information, one or more devices gathering environment information of an interior of a building, one or more devices gathering environment information from a moving vehicle, one or more anemometers, or a database corresponding to an enterprise organization.

15. The computing platform of claim 1, wherein the memory stores additional computer-readable instructions that, when executed by the at least one processor, cause the computing platform to:

cause, based on the determination, activation of an air filtration device corresponding to an installation location of the one or more environment information sources.

16. The computing platform of claim 1, wherein the memory stores additional computer-readable instructions that, when executed by the at least one processor, cause the computing platform to:

based on determining whether the cumulative particle score satisfies the criteria, updating an environmental profile to include an indication of whether the environment is a compliant environment.

17. The computing platform of claim 1, wherein the notification indicating the result of the determination comprises a haptic response.

18. A method comprising, by a computing platform comprising at least one processor, a communication interface, and memory:

training, based on historical sets of environment information, and known air compositions, an environment analysis model, wherein the training of the environment analysis model configures the environment analysis model to output estimated air compositions receiving, from one or more information sources and via the communication interface, a set of environment information corresponding to an environment, wherein the set of environment information comprises:

one or more measured variables corresponding to one or more attributes of a known particle, and one or more additional environment variables;

providing the one or more measured variables and the one or more additional environment variables as input to the environment analysis model to generate an estimated air composition;

generating, based on the estimated air composition, a cumulative particle score;

determining whether or not the cumulative particle score satisfies a criteria, wherein the criteria indicates whether the environment is a compliant environment or an outlier environment; and sending, based on the determination, one or more commands directing a user device to display a user interface, wherein the user interface comprises a notification indicating a result of the determination.

19. The method of claim 18, further comprising, by the computing platform:

determining, based on the set of environment information and using the environment analysis model, a source of one or more particles identified in the estimated air composition; and updating, based on the source of the one or more particles identified in the estimated air composition, the estimated air composition.

20. A system comprising a plurality of sensors and a computing platform:

wherein each sensor of the plurality of sensors comprises a transmitter and a detector, is located in a respective one of a plurality of geographic locations, and is configured to:

determine, using the detector, one or more measured variables corresponding to one or more attributes of a known particle in the respective one of the plurality of geographic locations of the sensor, and transmit information indicating the one or more measured variables and the one or more attributes of the known particle to the computing platform; and wherein the computing platform comprises a receiver, a processor, and a memory storing computer-readable instructions that, when executed by the processor, causes the computing platform to:

train, based on historical sets of environment information, and known air compositions, an environment analysis model, wherein training the environment analysis model configures the environment analysis model to output estimated air compositions;

receive, via the receiver, the information from each of the plurality of sensors;

receive an additional environment variable;

provide the one or more measured variables and the additional environment variable as input to the environment analysis model, to generate an estimated air composition of the plurality of geographic locations;

generate, based on the estimated air composition, a cumulative particle score;

determine, based on the estimated air composition, whether the plurality of geographic locations is a compliant environment or an outlier environment; and send, based on the determination of whether the plurality of geographic locations is a compliant environment or an outlier environment, one or more commands directing a user device to display a user interface, wherein the user interface comprises a notification indicating a result of the determination of whether the plurality of geographic locations is a compliant environment or an outlier environment.

* * * * *